(12) United States Patent
Abrecht et al.

(10) Patent No.: US 7,619,101 B2
(45) Date of Patent: Nov. 17, 2009

(54) PROCESS FOR THE PREPARATION OF (S)-4-FLUOROMETHYL-DIHYDRO-FURAN-2-ONE USEFUL IN THE PREPARATION OF THE DPP-IV INHIBITOR (S)-1 ((2S,3S,11BS)-2-AMINO-9,10-DIMETHOXY-1,3,4,6,7,11B-HEXAHYDRO-2H-PYRIDO[2,1-A]ISOQUINOLIN-3-YL)-4-FLUOROMETHYL-PYRROLIDIN-2-ONE

(75) Inventors: Stefan Abrecht, Duggingen (CH); Jean-Michel Adam, Reinach (CH); Alec Fettes, Zurich (CH); Joseph Foricher, Mulhouse (FR); Bruno Lohri, Reinach (CH); Patrizio Mattei, Riechen (CH); Gerard Moine, Riedisheim (FR); Rudolf Schmid, Basel (CH); Ulrich Zutter, Basel (CH)

(73) Assignee: Hoffman-La Roche Inc., Nutley, NJ (US)

( * ) Notice: Subject to any disclaimer, the term of this patent is extended or adjusted under 35 U.S.C. 154(b) by 432 days.

(21) Appl. No.: 11/438,034

(22) Filed: May 19, 2006

(65) Prior Publication Data
US 2006/0270853 A1  Nov. 30, 2006

(30) Foreign Application Priority Data
May 24, 2005  (EP)  ................. 05104408

(51) Int. Cl.
*C07D 307/00* (2006.01)
(52) U.S. Cl. .................................................. 549/324
(58) Field of Classification Search .................. 549/324
See application file for complete search history.

(56) References Cited

U.S. PATENT DOCUMENTS 5,274,125 A * 12/1993 Broger et al. ............... 549/216
6,545,165 B1  4/2003 Fleming et al.
7,307,037 B2 * 12/2007 Sannicolo' et al. .......... 502/162

FOREIGN PATENT DOCUMENTS

DE  101 57 533  6/2003
WO  WO 2005/000848  1/2005

OTHER PUBLICATIONS

Brieden et al, DN 133:209627, (1999).*
Experimental Chemistry, 4th edition, vol. 18, Organometallic complexes, pp. 339-344, Ed. Chemical Society of Japan, 1991, Maruzen.

B. Heiser et al., *Tetrahedron: Asymmetry* 1991, 2, 51.
N. Feiken et al., *Organometallics* 1997, 16, 537.
J.-P. Genet, *Acc. Chem. Res.* 2003, 36, 908.
Wang, Y et al, *Tetrahedron Ltrs*, 25:44 (1984) 4999-5002.
Huang, X. et al, *Organic Letters*, 4:25 (2002) 4419-4422.
Hughes, G. et al, *Jour. of the Amer. Chem. Soc*, vol. 125, (2003) p. 11253-11258 XP002394980.
Geiger, C. et al, *Advanced Synthesis and Catalysis*, vol. 347, 92005) pp. 249-254 XP002394981.
Schroer, J, Welzel, P., *Tetrahedron*, 50:22, (1994) pp. 6839-6858 XP002395005.

* cited by examiner

*Primary Examiner*—Janet L. Andres
*Assistant Examiner*—Raymond Covington
(74) *Attorney, Agent, or Firm*—George W. Johnston; Dennis P. Tramaloni; Samuel H. Megerditchian

(57) ABSTRACT

This invention relates to a process of the preparation of the novel intermediate (S)-4-fluoromethyl-dihydro-furan-2-one of the formula

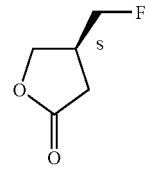

I and with its use for the manufacture of pyrido[2,1-a]isoquinoline derivatives of the formula

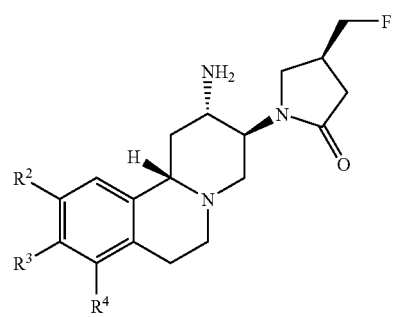

II which are useful for the treatment and/or prophylaxis of diseases which are associated with DPP IV.

21 Claims, No Drawings

PROCESS FOR THE PREPARATION OF (S)-4-FLUOROMETHYL-DIHYDRO-FURAN-2-ONE USEFUL IN THE PREPARATION OF THE DPP-IV INHIBITOR (S)-1 ((2S,3S,11BS)-2-AMINO-9,10-DIMETHOXY-1,3,4,6,7,11B-HEXAHYDRO-2H-PYRIDO[2,1-A]ISOQUINOLIN-3-YL)-4-FLUOROMETHYL-PYRROLIDIN-2-ONE

PRIORITY TO RELATED APPLICATIONS

This application claims the benefit of European Application No. 05104408.9, filed May 24, 2005, which is hereby incorporated by reference in its entirety.

FIELD OF THE INVENTION

The present invention relates to a process of the preparation of the novel intermediate (S)-4-fluoromethyl-dihydro-furan-2-one of the formula

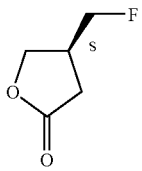

I and to its use for the manufacture of pyrido[2,1-a]isoquinoline derivatives of the formula

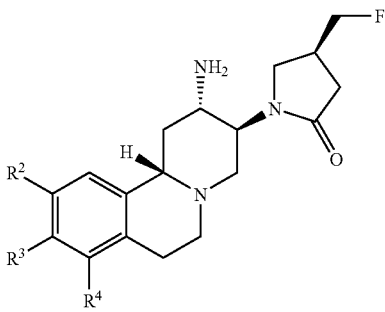

II which are useful for the treatment and/or prophylaxis of diseases which are associated with DPP IV.

All documents cited or relied upon below are expressly incorporated herein by reference.

BACKGROUND

The pyrido[2,1-a]isoquinoline derivatives of the formula

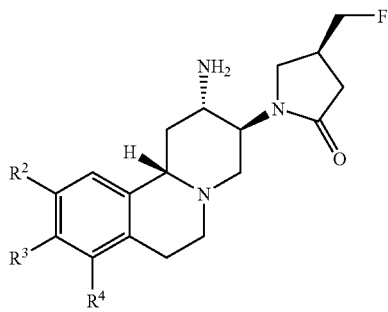

II wherein $R^2$, $R^3$ and $R^4$ are each independently selected from the group consisting of hydrogen, halogen, hydroxy, lower alkyl, lower alkoxy and lower alkenyl, wherein lower alkyl, lower alkoxy and lower alkenyl may optionally be substituted by a group consisting of lower alkoxycarbonyl, aryl and heterocyclyl, and the pharmaceutically acceptable salts thereof are disclosed in PCT International Patent Appl. WO 2005/000848.

A major task in the synthesis of the compounds of formula II is the introduction of the chiral (S)-4-fluoromethyl-pyrrolidino residue which in the current synthesis according to the PCT Int. Appl. WO 2005/000848 involves coupling of a suitably protected tricyclic amine moiety with a racemic side chain building block (i.e with rac-4-chloro-3-fluoromethyl-butyryl chloride) and isolation of the desired isomer from the ca. 1:1 isomer mixture by chromatographical separation. Such a chromatographical step is difficult to carry out on large technical scale and furthermore a yield of maximally ca. 50% can be achieved only. The problem to be solved therefore was to find a suitable process alternative which affords a higher yield and which can be conducted on technical scale.

SUMMARY OF THE INVENTION

In one embodiment of the present invention, provided is a process for the preparation of (S)-4-fluoromethyl-dihydro-furan-2-one of the formula

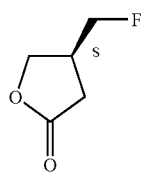

I comprising the step of converting a 4-fluoromethyl-5H-furan-2-one of the formula

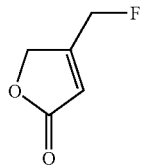   III by way of a catalytic asymmetric hydrogenation in the presence of a chiral catalyst.

In another embodiment of the present invention, provided is a compound of the formula

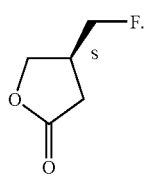   I

In a further embodiment of the present invention, provided is a compound of the formula

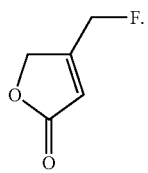   III

In a yet another embodiment of the present invention, provided is a process for the preparation of pyrido[2,1-a]isoquinoline derivatives of the formula

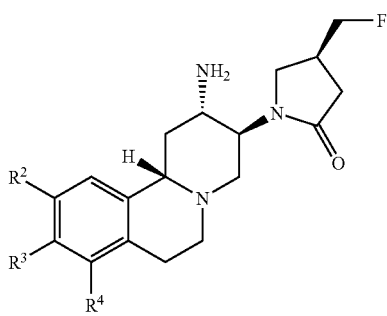   II wherein $R^2$, $R^3$ and $R^4$ are each independently selected from the group consisting of hydrogen, halogen, hydroxy, lower alkyl, lower alkoxy and lower alkenyl, wherein lower alkyl, lower alkoxy and lower alkenyl may optionally be substituted by a group selected from lower alkoxycarbonyl, aryl and heterocyclyl, comprising the process for the preparation of the formula I above, followed by coupling of the (S)-4-fluoromethyl-dihydro-furan-2-one of formula

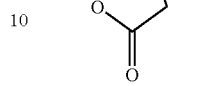   I with an amino-pyrido[2,1-a]isoquinoline derivative of formula

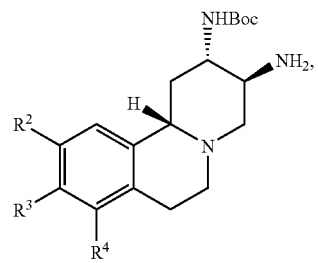   XIII wherein $R^2$, $R^3$ and $R^4$ are as defined above, cyclization of the obtained amide of formula

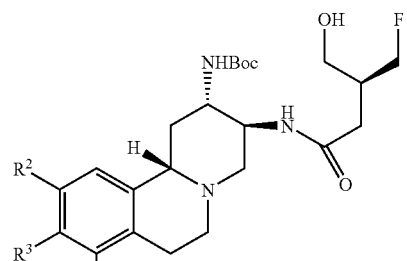   XIV in the presence of a base to obtain a compound of formula

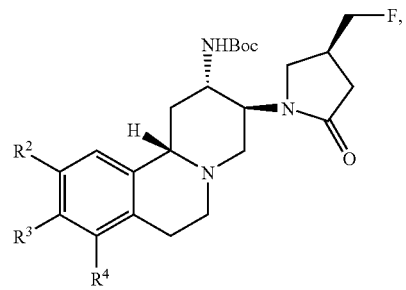   XV and deprotection of the amino group.

DETAILED DESCRIPTION

Unless otherwise indicated, the following definitions are set forth to illustrate and define the meaning and scope of the various terms used to describe the invention herein.

In this specification the term "lower" is used to mean a group consisting of one to six, preferably of one to four carbon atom(s).

The term "halogen" refers to fluorine, chlorine, bromine and iodine, with fluorine, bromine and chlorine being preferred.

The term "alkyl", alone or in combination with other groups, refers to a branched or straight-chain monovalent saturated aliphatic hydrocarbon radical of one to twenty carbon atoms, preferably one to sixteen carbon atoms, more preferably one to ten carbon atoms.

The term "lower alkyl", alone or in combination with other groups, refers to a branched or straight-chain monovalent alkyl radical of one to six carbon atoms, preferably one to four carbon atoms. This term is further exemplified by radicals such as methyl, ethyl, n-propyl, isopropyl, n-butyl, s-butyl, isobutyl, t-butyl, n-pentyl, 3-methylbutyl, n-hexyl, 2-ethylbutyl and the like. Preferable lower alkyl residues are methyl and ethyl, with methyl being especially preferred.

The term "halogenated lower alkyl" refers to a lower alkyl group as defined above wherein at least one of the hydrogens of the lower alkyl group is replaced by a halogen atom, preferably fluoro or chloro. Among the preferred halogenated lower alkyl groups are trifluoromethyl, difluoromethyl, fluoromethyl and chloromethyl.

The term "alkenyl" as used herein denotes an unsubstituted or substituted hydrocarbon chain radical having from 2 to 6 carbon atoms, preferably from 2 to 4 carbon atoms, and having one or two olefinic double bonds, preferably one olefinic double bond. Examples are vinyl, 1-propenyl, 2-propenyl (allyl) or 2-butenyl (crotyl).

The term "alkoxy" refers to the group R'—O—, wherein R' is alkyl. The term "lower-alkoxy" refers to the group R'—O—, wherein R' is a lower alkyl group as defined above. Examples of lower alkoxy groups are e.g. methoxy, ethoxy, propoxy, isopropoxy, butoxy, isobutoxy and hexyloxy, with methoxy being especially preferred.

The term "lower alkoxycarbonyl" refers to the group R'—O—C(O)—, wherein R' is a lower alkyl group as defined above.

The term "aryl" refers to an aromatic monovalent mono- or polycarbocyclic radical, such as phenyl or naphthyl, preferably phenyl, which may optionally be mono-, di- or tri-substituted, independently, by lower alkyl, lower alkoxy, halo, cyano, azido, amino, di-lower alkyl amino or hydroxy.

The term "cycloalkyl" refers to a monovalent carbocyclic radical of three to six, preferably three to five carbon atoms. This term is further exemplified by radicals such as cyclopropyl, cyclobutyl, cyclopentyl and cyclohexyl, with cyclopropyl and cyclobutyl being preferred. Such cycloalkyl residues may optionally be mono-, di- or tri-substituted, independently, by lower alkyl or by halogen.

The term "heterocyclyl" refers to a 5- or 6-membered aromatic or saturated N-heterocyclic residue, which may optionally contain a further nitrogen or oxygen atom, such as imidazolyl, pyrazolyl, thiazolyl, pyridyl, pyrimidyl, morpholino, piperazino, piperidino or pyrrolidino, preferably pyridyl, thiazolyl or morpholino. Such heterocyclic rings may optionally be mono-, di- or tri-substituted, independently, by lower alkyl, lower alkoxy, halo, cyano, azido, amino, di-lower alkyl amino or hydroxy. Preferable substituent is lower alkyl, with methyl being preferred.

The term "pharmaceutically acceptable salts" embraces salts of the compounds of formula II with inorganic or organic acids such as hydrochloric acid, hydrobromic acid, nitric acid, sulphuric acid, phosphoric acid, citric acid, formic acid, maleic acid, acetic acid, fumaric acid, succinic acid, tartaric acid, methanesulphonic acid, salicylic acid, p-toluenesulphonic acid and the like, which are non toxic to living organisms. Preferred salts with acids are formates, maleates, citrates, hydrochlorides, hydrobromides and methanesulfonic acid salts, with hydrochlorides being especially preferred.

In detail, the present invention refers to a process of the preparation of the novel intermediate (S)-4-fluoromethyl-dihydro-furan-2-one of the formula

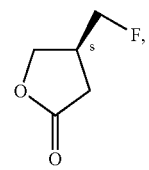

I comprising the conversion of 4-fluoromethyl-5H-furan-2-one of the formula

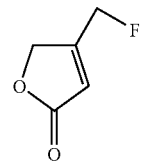

III by way of a catalytic asymmetric hydrogenation in the presence of a chiral catalyst.

Preferably, the chiral catalyst is selected is selected from a ruthenium or a rhodium complex catalyst containing a chiral diphosphine ligand.

In a preferred embodiment of the present invention, the chiral diphosphine ligand is a compound selected from the group consisting of formula IV, V, VI, VII and VIII:

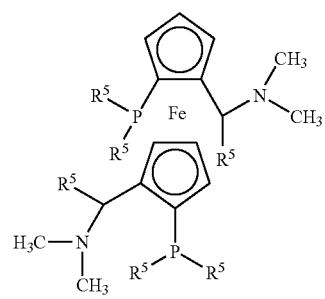

IV

-continued

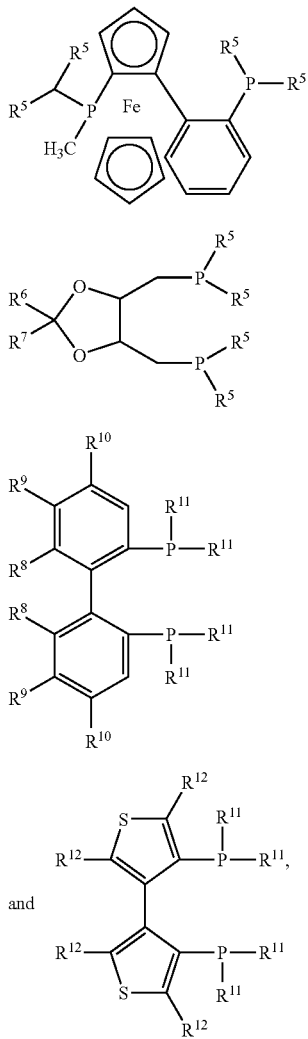

V

VI

VII

VIII and wherein

R⁵ independently from each other is aryl, heteroaryl, cylcoalkyl or lower alkyl;

R⁶ is lower alkyl;

R⁷ is lower alkyl;

R⁸ is lower alkyl, lower alkoxy, hydroxy or —O—C(O)-lower alkyl;

R⁹ and R¹⁰ independently from each other are hydrogen, lower alkyl, lower alkoxy or lower dialkylamino; or R⁸ and R⁹ which are attached to the same phenyl group, or R⁹ and R¹⁰ which are attached to the same phenyl group, or both R⁸, taken together, are —X—(CH₂)ₙ—Y—, wherein X is —O— or —C(O)O—, Y is —O— or —N(lower alkyl)- and n is an integer from 1 to 6; or R⁸ and R⁹, or R⁹ and R¹⁰, together with the carbon atoms to which they are attached, form a naphthyl, tetrahydronaphthyl or dibenzofuran ring;

R¹¹ independently from each other is selected from the group consisting of unsubstituted phenyl, phenyl substituted by 1 to 5 substituents independently selected from the group consisting of lower alkyl, lower alkoxy, lower dialkylamino, morpholino, phenyl and lower trialkylsilyl, unsubstituted naphthyl, and napthyl substituted by 1 to 7 substituents independently selected from the group consisting of lower alkyl, lower alkoxy, lower dialkylamino, morpholino, phenyl and lower trialkylsilyl; and R¹² independently from each other is lower alkyl.

If R¹¹ is phenyl, it is preferably unsubstituted or substituted by 1 to 3 substituents as described above.

Preferred catalysts are selected from a rhodium complex catalyst containing a chiral diphosphine ligand selected from the group consisting of (S)-(+)-TMBTP, (S)-BINAP, (S)-MeOBIPHEP, (S)-BIPHEMP, (S)-Synphos, (S)-Solphos, (S)-(3-Thienyl)-MeOBIPHEP, (S)-3,5-tBu-MeOBIPHEP, (S)-3,5-Xyl-MeOBIPHEP, (S)-(S)-Walphos, (S)-(R)—NMe₂-PPh₂-Mandyphos, and (S,S)-DIOP, or from a ruthenium complex catalyst containing a chiral diphosphine ligand selected from the group consisting of (R)-BINAP, (R)-p-Tol-BINAP, (R)-MeOBIPHEP, (R)-BIPHEMP, (R)-BIPHOMP, (R)-DiMeOBIPHEP, (R)-3,5-tBu-MeOBIPHEP, (R)-BIBFUB, (R)-(3,5-Xyl-MeOBIPHEP)(S-DAIPEN), (R)-3,5-iPr-MeOBIPHEP, (R)-3,5-iPr, 4-MeO-MeOBiPHEP, and (R)-3,5-tBu, 4-MeO-MeOBIPHEP.

Each of these chiral diphosphines individually constitute a preferred embodiment of the present invention.

Especially preferred catalysts are a rhodium complex catalyst containing (S)-(+)-TMBTP as chiral diphosphine ligand or a ruthenium complex catalyst containing (R)-3,5-tBu-MeOBIPHEP or (R)-3,5-iPr-MeOBIPHEP as chiral diphosphine ligand. Most preferred among the rhodium catalysts is the rhodium complex catalyst containing (S)-(+)-TMBTP as chiral diphosphine ligand and most preferred among the ruthenium catalysts is the ruthenium complex catalyst containing (R)-3,5-tBu-MeOBIPHEP as chiral diphosphine ligand.

In the rhodium complex catalysts referred to above, rhodium is characterised by the oxidation number I. Such rhodium complexes can optionally comprise further ligands, either neutral or anionic.

Examples of such neutral ligands are e.g. olefins, e.g. ethylene, propylene, cyclooctene, 1,3-hexadiene, 1,5-hexadiene, norbornadiene (nbd=bicyclo-[2.2.1]hepta-2,5-diene), (Z,Z)-1,5-cyclooctadiene (cod) or other dienes which form readily soluble complexes with rhodium or ruthenium, benzene, hexamethylbenzene, 1,3,5-trimethylbenzene, p-cymene, or also solvents such as e.g. tetrahydrofuran, dimethylformamide, acetonitrile, benzonitrile, acetone, methanol and pyridine.

Examples of such anionic ligands are halides or the group A—COO, wherein A represents lower alkyl, aryl, halogenated lower alkyl or halogenated aryl. Preferably, A—COO is $CH_3COO^-$ or $CF_3COO^-$. If the rhodium complex is charged, non coordinating anions such as a halide, $BF_4^-$, $ClO_4^-$, $SbF_6^-$, $PF_6^-$, $B(phenyl)_4^-$, $B(3,5\text{-di-trifluoromethyl-phenyl})_4^-$, $CF_3SO_3^-$, $C_6H_5SO_3^-$ are present.

Preferred catalysts comprising rhodium and a chiral diphosphine are of the formula

[Rh(chiral diphosphine)LX]   IX wherein X is a halide such as $Cl^-$, $Br^-$ or $I^-$, and L is a neutral ligand as defined above. If L is a ligand comprising two double bonds, e.g. 1,5-cyclooctadiene, only one such L is present. If L is a ligand comprising only one double bond, e.g. ethylene, two such L are present.

A rhodium complex catalyst can be prepared, for example, by reaction of rhodium precursors such as e.g. di-$\eta^4$-chloro-bis[$\eta^4$-(Z,Z)-1,5-cyclo-octadiene]dirhodium(I) ([Rh(cod)Cl]$_2$), di-$\mu$-chloro-bis[$\eta^4$-norbornadiene]-dirhodium(I) ([Rh(nbd)Cl]$_2$), bis[$\eta^4$-(Z,Z)-1,5-cyclooctadiene]rhodium tetrafluoroborate ([Rh(cod)$_2$]BF$_4$) or bis[$\eta^4$-(Z,Z)-cyclooctadiene]rhodium perchlorate ([Rh(cod)$_2$]ClO$_4$) with a chiral diphosphine ligand in a suitable inert organic or aqueous solvent (e.g. according to the method described in *Experimental Chemistry*, 4$^{th}$ edition, Vol. 18, Organometallic complexes, pp. 339-344, Ed. Chemical Society of Japan, 1991, Maruzen).

In the ruthenium complex catalysts referred to above, ruthenium is characterised by the oxidation number II. Such ruthenium complexes can optionally comprise further ligands, either neutral or anionic. Examples of such neutral ligands are e.g. olefins, e.g. ethylene, propylene, cyclooctene, 1,3-hexadiene, norbornadiene, 1,5-cyclooctadiene, benzene, hexamethylbenzene, 1,3,5-trimethylbenzene, p-cymene, or also solvents such as e.g. tetrahydrofuran, dimethylformamide, acetonitrile, benzonitrile, acetone and methanol. Examples of such anionic ligands are $CH_3COO^-$, $CF_3COO^-$ or halides. If the ruthenium complex is charged, non coordinating anions such as halides, $BF_4^-$, $ClO_4^-$, $SbF_6^-$, $PF_6^-$, $B(phenyl)_4^-$, $B(3,5\text{-di-trifluoromethyl-phenyl})_4^-$, $CF_3SO_3^-$, $C_6H_5SO_3^-$ are present.

Suitable ruthenium complexes in question can be represented e.g. by the following formula Ru(Z)$_2$D   X wherein Z represents halogen or the group A—COO, A represents lower alkyl, aryl, halogenated lower alkyl or halogenated aryl and D represents a chiral diphosphine ligand.

These complexes can in principle be manufactured in a manner known per se, e.g. according to B. Heiser et al., *Tetrahedron: Asymmetry* 1991, 2, 51 or N. Feiken et al., *Organometallics* 1997, 16, 537 or J.-P. Genet, *Acc. Chem. Res.* 2003, 36, 908 and references cited therein.

Conveniently and preferably, ruthenium complexes are manufactured, for example, by reacting a complex of the formula

[Ru(Z$^1$)$_2$L$^1_m$]$_p$·(H$_2$O)$_q$   XI wherein Z$^1$ represents halogen or a group A$^1$—COO, A$^1$ represents lower alkyl or halogenated lower alkyl, L$^1$ represents a neutral ligand as defined above, m represents the number 1, 2 or 3, p represents the number 1 or 2 and q represents the number 0 or 1, with a chiral diphosphine ligand. Where m represents the number 2 or 3, the ligands can be the same or different.

Typically, ruthenium catalysts exemplified within the present invention can be prepared according to the method described by M. P. Fleming et al., U.S. Pat. No. 6,545,165 B1, for the preparation of chiral ruthenium dicarboxylate diphosphines.

Rhodium or ruthenium complex catalysts as described above can also be prepared in situ, i.e. just before use and without isolation. The solution in which such a catalyst is prepared can already contain the substrate for the enantioselective hydrogenation or the solution can be mixed with the substrate just before the hydrogenation reaction is initiated.

The asymmetric hydrogenation of a compound of formula III according to the present invention takes place at a hydrogen pressure in a range from 1 bar to 120 bar. Preferably, the asymmetric hydrogenation is carried out at a pressure of 1 bar to 20 bar. Most preferably, a hydrogen pressure of 3 bar to 7 bar is used. The reaction temperature is conveniently chosen in the range of 0° C. to 120° C. A process, wherein the asymmetric hydrogenation is carried out at a reaction temperature from 20° C. to 70° C., is preferred. This reaction can be effected in an inert organic solvent such as dichloromethane, methanol, ethanol, n-propanol, isopropanol, 2,2,2-trifluoroethanol, benzotrifluoride (Ph-CF$_3$), tetrahydrofuran, ethyl acetate or toluene, or mixtures of such solvents. Preferably, the rhodium catalyzed hydrogenation is carried out in dichloromethane or benzotrifluoride and the ruthenium catalyzed hydrogenation is carried out in a solvent taken from the group consisting of 2,2,2-trifluoroethanol, methanol, ethanol, n-propanol and dichloromethane, or mixtures of these solvents. More preferably, the ruthenium catalyzed hydrogenation is carried out in 2,2,2-trifluoroethanol or methanol.

A further embodiment of the present invention is the product of the asymmetric hydrogenation, i.e. the (S)-4-fluoromethyl-dihydro-furan-2-one of the formula

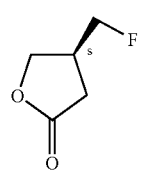

I and the (S)-4-fluoromethyl-dihydro-furan-2-one as component of an enantiomeric mixture of (S) and (R)-4-fluoromethyl-dihydro-furan-2-one having an enantiomeric ratio of the (S)- to (R)-isomer of at least 70:30, more preferably of at least 90:10.

The invention further relates to the educt of the asymmetric hydrogenation, which is the 4-fluoromethyl-5H-furan-2-one of the formula

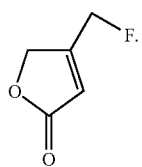

III

The preparation of the 4-fluoromethyl-5H-furan-2-one can be performed according to schemes 1 or 2 below.

2,2,6,6-tetramethyl-1-piperidinyloxy radical (TEMPO). In a next step 1-tert-butoxy-3-fluoro-propan-2-one (7) is reacted with tert-butyl acetate in the presence of a strong base such as lithium diisopropylamine (LDA) to form 3-tert-butoxymethyl-4-fluoro-3-hydroxybutyric acid tert-butyl ester (8) which can be cyclizised to 4-fluoromethyl-4-hydroxy-dihydro-furan-2-one (9) under strong acidic conditions (e.g. by employing trifluoroacetic acid or sulfuric acid 95%). Preferably, the cyclization is carried out with only a small amount of sulfuric acid 95% (e.g. 0.025 mol equivalent in relation to the educt) in a solvent such as 1,2-dimethoxyethane or dioxane. These two last steps can alternatively be carried out in a one-pot procedure, e.g. without isolating 3-tert-butoxymethyl-4-fluoro-3-hydroxybutyric acid tert-butyl ester (8). In a final step 4-fluoromethyl-5H-furan-2-one (III) is obtained by Scheme 1

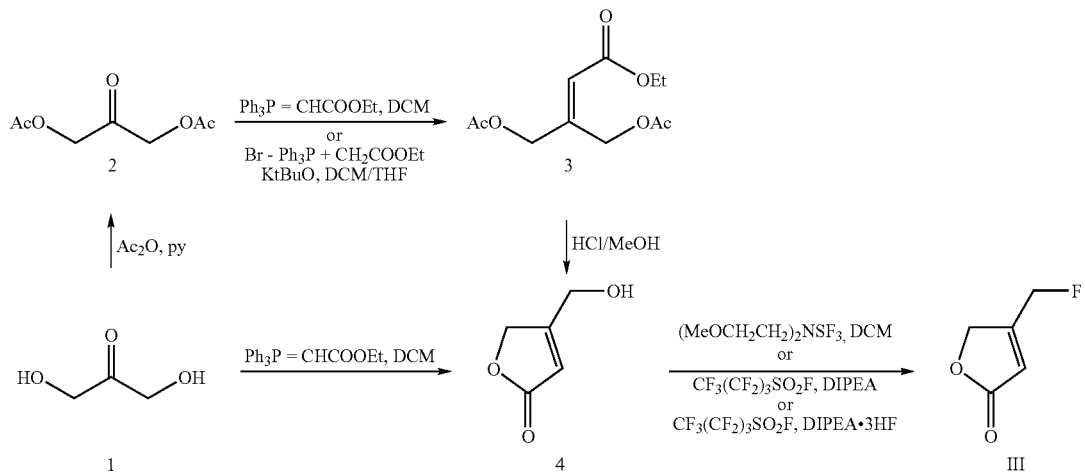

Dihydroxyacetone (1) is in a first step diacetylated to form the 3-acetoxy-2-oxo-propylester (2) which by a Wittig-reaction with carbethoxymethylene triphenyl phosphorane is converted to the 4-acetoxy-3-acetoxymethyl-but-2-enoic acid ethyl ester (3). Cyclization in the presence of hydrochloric acid provides the 4-hydroxymethyl-5H-furan-2-one (4). Alternatively, 4-hydroxymethyl-5H-furan-2-one (4) can be obtained by direct reaction of dihydroxyacetone (1) with the Wittig reagent carbethoxymethylene triphenylphosphorane. Conversion of 4-hydroxymethyl-5H-furan-2-one (4) into the desired 4-fluoromethyl-5H-furan-2-one of the formula III can be performed by reaction with a suitable deoxyfluorination reagent such as bis-(2-methoxyethyl)aminosulfur trifluoride or perfluorobutanesulfonyl fluoride in the presence of a trialkylamine base such as diisopropylethylamine (DIPEA). The reaction with perfluorobutanesulfonyl fluoride is advantageously performed in the presence of a trialkylamine tris (hydrofluoride) such as diisopropylethylamine (trishydrofluoride).

Starting from 2-tert-butoxymethyl-oxirane (5), 4-fluoromethyl-5H-furan-2-one can be prepared according to the method described in scheme 2. In the first step, the oxirane ring is opened with potassium hydrogendifluoride to form 1-tert-butoxy-3-fluoro-propan-2-ol (6) which is then oxidized to the corresponding ketone (7). The oxidation can be carried out according to known methods such as e.g. with sodium hypochlorite in the presence of a catalyst such as dehydration of 4-fluoromethyl-4-hydroxy-dihydro-furan-2-one (9). The dehydration can be performed according to known methods, e.g with acetic anhydride in the presence of an amine base such as triethylamine. Alternative dehydration methods include the use of thionyl chloride in the presence of pyridine or mesyl chloride in the presence of triethylamine. In a further alternative dehydration method, 4-fluoromethyl-4-hydroxy-dihydro-furan-2-one (9) is reacted with acetic anhydride to form the intermediate 4-acetoxy-fluoromethyl-dihydro-furan-2-one which is then reacted with sodium acetate in de-ionized water to obtain the compound of formula III.

Scheme 2

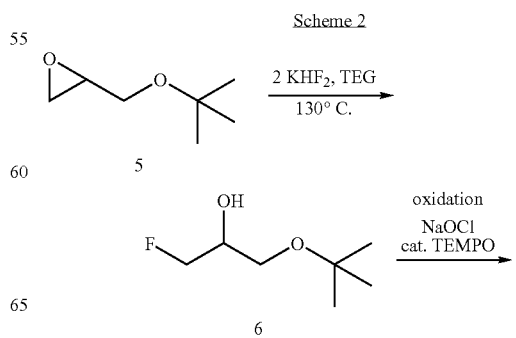

-continued

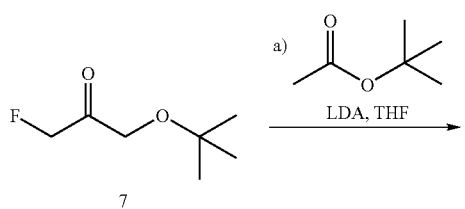
7

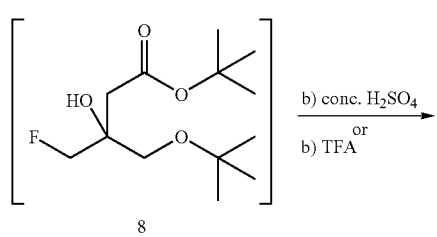
8

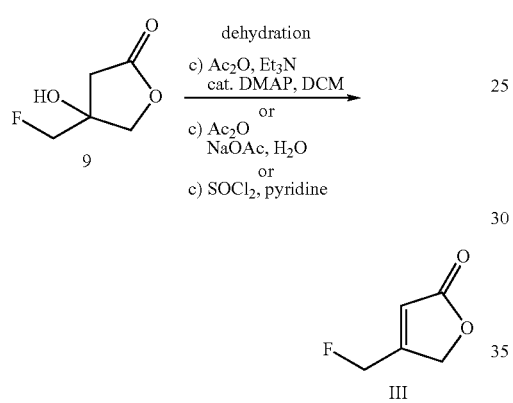
9

The invention further relates to the use of the 4-fluoromethyl-5H-furan-2-one of the formula

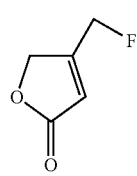
III for the preparation of the (S)-4-fluoromethyl-dihydro-furan-2-one of the formula

I

More specifically, the invention relates to the use of the 4-fluoromethyl-5H-furan-2-one of the formula

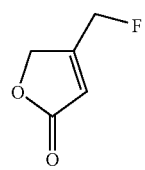
III for the preparation of for the preparation of pyrido[2,1-a]isoquinoline derivatives of the formula

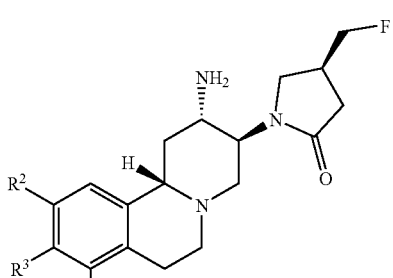
II wherein $R^2$, $R^3$ and $R^4$ are each independently selected from the group consisting of hydrogen, halogen, hydroxy, lower alkyl, lower alkoxy and lower alkenyl, wherein lower alkyl, lower alkoxy and lower alkenyl may optionally be substituted by a group selected from lower alkoxycarbonyl, aryl and heterocyclyl;

and of pharmaceutically acceptable salts thereof.

Preferably, the invention relates to the use of the 4-fluoromethyl-5H-furan-2-one of the formula III for the preparation of (S)-1-((2S,3S,11bS)-2-amino-9,10-dimethoxy-1,3,4,6,7,11b-hexahydro-2H-pyrido[2,1-a]isoquinolin-3-yl)-4-fluoromethyl-pyrrolidin-2-one.

In a further embodiment of the present invention the (S)-4-fluoromethyl-dihydro-furan-2-one of formula

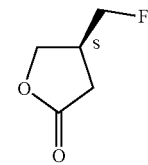
I or an enantiomeric mixture of the (S)- and (R)-isomer of 4-fluoromethyl-dihydro-furan-2-one can be used for the preparation of pyrido[2,1-a]isoquinoline derivatives of the formula

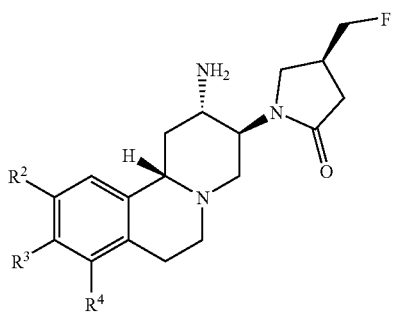

II wherein $R^2$, $R^3$ and $R^4$ are each independently selected from the group consisting of hydrogen, halogen, hydroxy, lower alkyl, lower alkoxy and lower alkenyl, wherein lower alkyl, lower alkoxy and lower alkenyl may optionally be substituted by a group selected from lower alkoxycarbonyl, aryl and heterocyclyl, and of pharmaceutically acceptable salts thereof, according to the following schemes:

Scheme 3

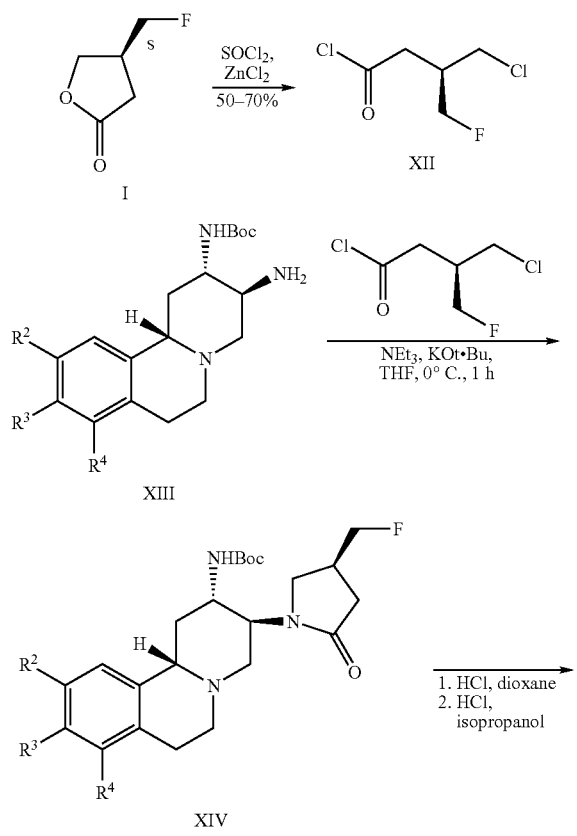

-continued

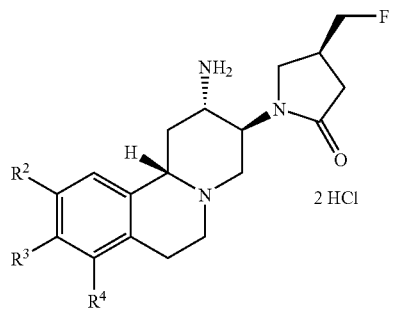

II

The (S)-4-fluoromethyl-dihydro-furan-2-one can be ring opened in the presence of zinc chloride and thionyl chloride to provide the respective (R)-4-chloro-3-fluoromethyl-butyryl chloride (XII). The acid chloride can then be coupled with the amino-pyrido[2,1-a]isoquinoline derivative (XIII) to form the fluoromethyl-pyrrolidin-2-one derivative of the pyrido[2,1-a]isoquinoline (XIV) which after deprotection yields the desired pyrido[2,1-a]isoquinoline derivative (II) (Scheme 3).

Scheme 4

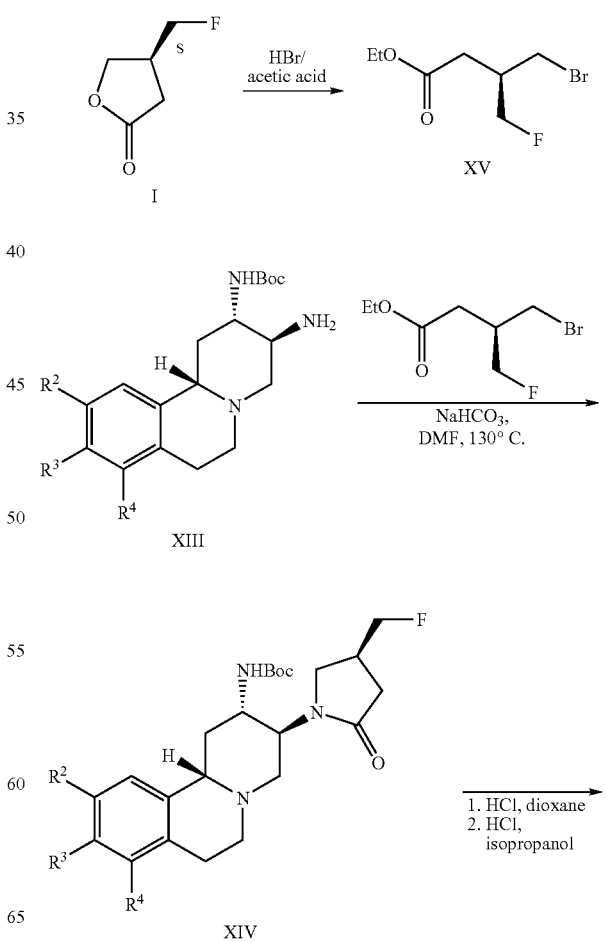

-continued

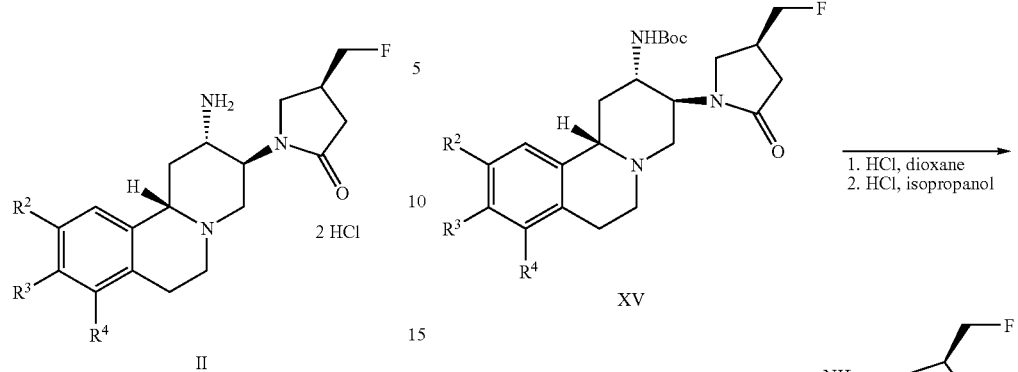

According to another embodiment (Scheme 4) the (S)-4-fluoromethyl-dihydro-furan-2-one is ring opened in the presence of HBr/acetic acid to provide the respective (R)-4-bromo-3-fluoromethyl-butyric acid ethyl ester (XV). This ester can then be coupled with the amino-pyrido[2,1-a]isoquinoline derivative (XIII) to form the fluoromethyl-pyrrolidin-2-one derivative of the pyrido[2,1-a]isoquinoline (XIV) which after deprotection yields the desired pyrido[2,1-a]isoquinoline derivative (II).

Scheme 5

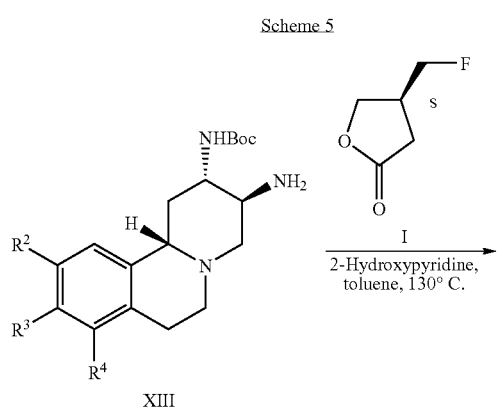

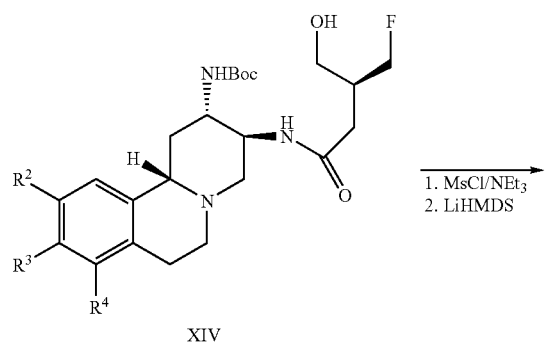

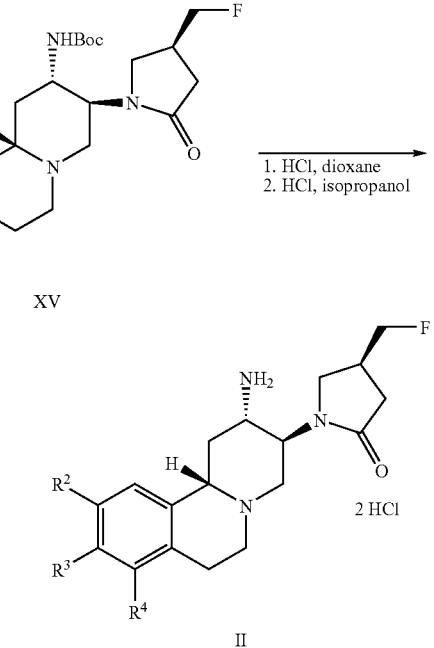

According to still another embodiment (Scheme 5) the (S)-4-fluoromethyl-dihydro-furan-2-one is directly coupled with the amino-pyrido[2,1-a]isoquinoline derivative (XIII) to form the hydroxymethyl derivative of the pyrido[2,1-a]isoquinoline (XIV), which was subsequently cyclized to the fluoromethyl-pyrrolidin-2-one derivative (XV). The latter can be deprotected to yield the desired pyrido[2,1-a]isoquinoline derivative (II).

Preferably, the invention relates to a process for the preparation of (S)-1-((2S,3S,11bS)-2-amino-9,10-dimethoxy-1,3,4,6,7,11b-hexahydro-2H-pyrido[2,1-a]isoquinolin-3-yl)-4-fluoromethyl-pyrrolidin-2-one, comprising the process for the preparation of (S)-4-fluoromethyl-dihydro-furan-2-one as described herein before, followed by coupling of the (S)-4-fluoromethyl-dihydro-furan-2-one of formula

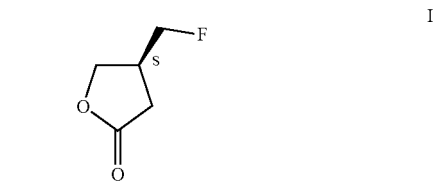

with (2S,3S,11bS)-3-amino-9,10-dimethoxy-1,3,4,6,7,11b-hexahydro-2H-pyrido[2,1-a]isoquinolin-2-yl)-carbamic acid tert-butyl ester, cyclization of the obtained (2S,3S,11bS)-3-(3-fluoromethyl-4-hydroxy-butyrylamino)-9,10-dimethoxy-1,3,4,6,7,11b-hexahydro-2H-pyrido[2,1-a]isoquinolin-2-yl]-carbamic acid tert-butyl ester in the presence of a base, and deprotecting the obtained (2S,3S,11bS)-3-((4S)-fluoromethyl-2-oxo-pyrrolidin-1-yl)-9,10-dimethoxy-1,3,4,6,7,11b-hexahydro-2H-pyrido[2,1-a]isoquinolin-2-yl]-carbamic acid tert-butyl ester.

Thus, in a preferred embodiment, the invention relates to the use of the (S)-4-fluoromethyl-dihydro-furan-2-one of the formula

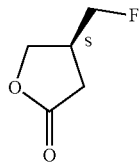

or of an enantiomeric mixture of (S) and (R)-4-fluoromethyl-dihydro-furan-2-one having an enantiomeric ratio of the (S)- to (R)-isomer of at least 70:30, more preferably of at least 90:10, for the preparation of a pyrido[2,1-a]isoquinoline derivative of the formula

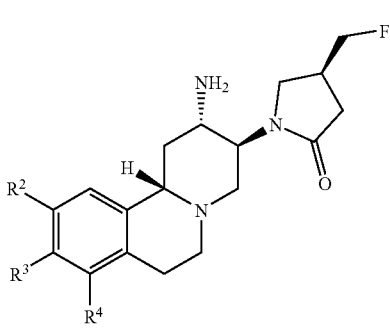

wherein $R^2$ and $R^3$ are methoxy and $R^4$ is hydrogen.

The pyrido[2,1-a]isoquinoline derivatives of formula (II) as disclosed in the PCT Int. Application WO 2005/000848 are useful for the treatment and/or prophylaxis of treatment and/or prophylaxis of diseases which are associated with DPP IV such as diabetes, particularly non-insulin dependent diabetes mellitus, and/or impaired glucose tolerance, as well as other conditions wherein the amplification of action of a peptide normally inactivated by DPP-IV gives a therapeutic benefit. Surprisingly, the compounds of the present invention can also be used in the treatment and/or prophylaxis of obesity, inflammatory bowel disease, Colitis Ulcerosa, Morbus Crohn, and/or metabolic syndrome or β-cell protection. Furthermore, the compounds of the present invention can be used as diuretic agents and for the treatment and/or prophylaxis of hypertension. Unexpectedly, the compounds of the present invention exhibit improved therapeutic and pharmacological properties compared to other DPP-IV inhibitors known in the art, such as e.g. in context with pharmacokinetics and bioavailability.

The following examples shall illustrate the invention without limiting it.

EXAMPLES

Abbreviations

DMF=dimethylformamide, (S)-DAIPEN=1,1-bis(4-methoxyphenyl)-3-methyl-1,2-butanediamine (commercially available from Strem Chemicals Inc.), R,R-DPEN=(1R,2R)-(+)-1,2-Diphenylethylenediamine (commercially available from Strem Chemicals Inc.), RT=room temperature, TBME=tert.-butyl methyl ether, THF=tetrahydrofuran.

Acronyms of Diphosphine Ligands

| | |
|---|---|
| (S)-(+)-TMBTP | (S)-4,4'-Bis(diphenylphosphino)-2,2',5,5'-tetramethyl-3,3'-dithiophene (CAS Reg. No. 175871-48-4; synthesis described by T. Benincori et al., J. Org. Chem. 2000, 65, 2043, see also International Patent Application WO 96/01831) |
| BINAP [1] | 2,2'-Bis(diphenylphosphino)-1,1'-binaphthyl (commercially available from Fluka) |
| MeOBIPHEP [1] | (6,6'-Dimethoxybiphenyl-2,2'-diyl)bis(diphenylphosphine) (commercially available from Fluka) |
| BIPHEMP [1] | (6,6'-Dimethylbiphenyl-2,2'-diyl)bis(diphenylphosphine) (CAS Reg. No.'s 91548-06-0 (R) or 91548-08-2 (S)) |
| (S)-Synphos | (S)-(2,2',3,3'-tetrahydro[5,5'-bi-1,4-benzodioxin]-6,6'-diyl)bis(diphenylphosphine) (CAS Reg. No. 503538-68-9; synthesis described by S. Duprat de Paule et al., Org. Proc. Res. Dev. 2003, 7, 399) |
| (S)-Solphos | (S)-N,N'-Dimethyl-7,7'-bis(diphenylphosphino)-3,3',4,4'-tetrahydro-8,8'-bi-2H-1,4-benzoxazine, (commercially available from Strem Chemicals Inc.) |
| 3-Thienyl-MeOBIPHEP [1] | (6,6'-Dimethoxy[1,1'-biphenyl]-2,2'-diyl)bis[bis(3-thienyl)phosphine |
| 3,5-tBu-MeOBIPHEP [1] | (6,6'-Dimethoxy[1,1'-biphenyl]-2,2'-diyl)bis(bis(3,5-di-tert.-butylphenyl)phosphine |
| 3,5-tBu, 4-MeO-MeOBIPHEP [1] | (6,6'-Dimethoxy[1,1'-biphenyl]-2,2'-diyl)bis(bis(3,5-di-tert.-butyl-4-methoxyphenyl)phosphine |
| 3,5-iPr-MeOBIPHEP [1] | (6,6'-Dimethoxy[1,1'-biphenyl]-2,2'-diyl)bis(bis(3,5-di-isopropylphenyl)phosphine |
| 3,5-iPr, 4-MeO-MeOBIPHEP [1] | (6,6'-Dimethoxy[1,1'-biphenyl]-2,2'-diyl)bis(bis(3,5-di-isopropyl-4-methoxyphenyl)phosphine |
| 3,5-Xyl-MeOBIPHEP [1] | [6,6'-Dimethoxy[1,1'-biphenyl]-2,2'-diyl]bis[bis(3,5-dimethylphenyl)phosphine (CAS Reg. No. 394248-45-4 (R)) |
| (R,R)-DIOP | [[(4R,5R)-2,2-Dimethyl-1,3-dioxolane-4,5-diyl]bis(methylene)]bis(diphenylphosphine) (commercially available from Fluka) |
| (R)-p-Tolyl-BINAP [1] | (R)-[1,1'-Binaphthalene]-2,2'-diylbis(bis(4-methylphenyl)-phosphine) (CAS Reg. No. 99646-28-3) |
| (R)-BIPHOMP | [(11aR)-5,7-Dihydrodibenz[c,e]oxepin-1,11-diyl]bis(diphenylphosphine) (CAS Reg. No. 121843-13-8; synthesis described by R. Schmid et al., Helv. Chim. Acta 1988, 71, 897) |
| DiMeOBIPHEP [1] | (5,5',6,6'-Tetramethoxy[1,1'-biphenyl]-2,2'-diyl)bis(diphenyl-phosphine) (CAS Reg. No.'s 133545-20-7 (S) or 133545-19-4 (R)) |
| NMe2-PPh2-Mandyphos | 1,1'-Bis[(dimethylamino)phenylmethyl]-2,2'-bis(diphenyldiphosphino)-ferrocene (commercially available from Strem Chemicals Inc.) |
| Walphos | 1-[(1R)-1-[Bis[3,5-bis(trifluoromethyl)-phenyl]phosphino]ethyl]-2-[2-(diphenylphosphino)phenyl]-ferrocene (commercially available from Strem Chemicals Inc.) |
| (R)-BIBFUP | (R)-[4,4'-Bidibenzofuran]-3,3'-diylbis(diphenylphosphine) (CAS Reg. No. 165534-89-4; preparation described in European Patent Application EP 0 643 065) |
| (S)-DAIPEN | 1,1-Bis(4-methoxyphenyl)-3-methyl-1,2-butanediamine (commercially available from Strem Chemicals Inc.) |

These ligands are known and/or can be prepared according to the examples or methods as described in patent application documents EP 0 398 132, WO 92/16535, EP 0 104 375 or EP 0580331.

Example 1

Preparation of acetic acid 3-acetoxy-2-oxo-propyl ester

A 16 L reactor equipped with a mechanical stirrer, a Pt-100 thermometer, a reflux condenser and a nitrogen inlet was charged with 1.00 kg (10.9 mol) 1,3-dihydroxyacetone and 3.25 L (4.03 mol) pyridine. To this suspension 3.31 L (34.8 mol) acetic acid anhydride was added during 35 min, maintaining the temperature between 15 and 22° C. with a cooling bath. During the addition the suspension turned into a clear, slightly reddish solution. The mixture was stirred for 2.5 h at RT before it was concentrated on a rotatory evaporator at 50-55° C./10 mbar. The oily residue was dissolved in 10.0 L dichloromethane and washed two times with 5.0 L 2N hydrochloric acid, then with 5.0 L water. The organic layer was concentrated on a rotatory evaporator at 40° C./10 mbar and the oily residue was further dried under these conditions for 1.5 h. The dark red crude product (2 kg) was dissolved in 5.7 L toluene and the solution was warmed to 30° C. 5 L heptane were added during 10 min and the resulting turbid solution was seeded with product crystals, whereas fast crystallization occurred. 5 L heptane was added to the suspension to improve stirability. After stirring overnight at RT the suspension was cooled to 0° C. and stirred for 2 h at that temperature. The crystals then were filtered off and washed portionwise with totally 7 L of pre-cooled heptane. The crystals were dried at 30-35° C. at <=10 mbar over the weekend, to give 1.47 kg 1,3-diacetoxyacetone (78% yield; assay: 100%).

Example 2

Preparation of carbethoxymethylene triphenylphosphorane

A 4.5 L reactor equipped with a mechanical stirrer, a Pt-100 thermometer, a dropping funnel and a nitrogen inlet was charged with 450 g (1.03 mol) ethoxycarbonylmethyltriphenyl phosphonium bromide, 1.0 L dichloromethane and 1.5 L water. The two-phase mixture was cooled to 5° C. and 565 ml (1.13 mol) 2N sodium hydroxide solution was added during 30 min, maintaining the temperature between 3 and 7° C. After completed addition the mixture was stirred for 75 min at that temperature, then the phases were separated, the aqueous layer extracted with 500 ml dichloromethane and the combined organic layers were concentrated on a rotatory evaporator at 50° C./10 mbar to give 363 g crude product as slightly brownish crystals. These were dissolved in 450 ml dichloromethane under reflux. Ca. 1.35 L heptane were added during 30 min to the refluxing mixture until a slight turbidity persisted. After 1 h at 40-45° C. the mixture was seeded with product crystals and the suspension was allowed to cool to 30-32° C. during 3 h. At that point another 450 mL heptane were added and the mixture was stirred overnight at RT, followed by 2 h at 0-4° C. The crystals were filtered off, washed with 450 mL pre-cooled heptane and dried overnight at 45° C./10 mbar, to give 310 g carbethoxymethylene triphenylphosphorane (98% yield; assay: 98.4%) as white crystals.

Example 3

Preparation of 4-acetoxy-3-acetoxymethyl-but-2-enoic acid ethyl ester

A 3.5 L reactor equipped with a mechanical stirrer, a Pt-100 thermometer and a nitrogen inlet was charged with 127 g (731 mmol) 1,3-diacetoxyacetone, 1.95 L TBME and 309 g (877 mmol) carbethoxymethylene triphenylphosphorane. The solution was refluxed for 5 h, then allowed to cool to RT during 14 h. Then TBME was exchanged with 2.3 L heptane at 40° C./300 mbar and the mixture was stirred overnight at RT before 400 ml toluene was added. The suspension was stirred for 1 h at RT, then 2 h at 0-4° C., filtered, and the filter cake was washed portionwise with totally 600 ml pre-cooled toluene. The combined filtrates were concentrated on a rotatory evaporator at 45° C./10 mbar to give 193 g crude product as reddish oil. This material was dissolved in 200 ml of a heptane/ethyl acetate (3:1) mixture and was chromatographically filtered over a column containing 400 g silica gel 60 using heptane/ethyl acetate (3:1) as the eluent, to give 174 g 4-acetoxy-3-acetoxymethyl-but-2-enoic acid ethyl ester (98% yield; assay: 99.9%) as a colorless oil.

Example 4

Example 4a

Preparation of 4-hydroxymethyl-5H-furan-2-one

In a 1.5 L reactor equipped with a mechanical stirrer, a Pt-100 thermometer, a dropping funnel and a nitrogen inlet, 174 g (714 mmol) 4-acetoxy-3-acetoxymethyl-but-2-enoic acid ethyl ester was dissolved in 810 mL methanol. 5.05 mL (71 mmol) acetyl chloride was added during 10 min under slight cooling, maintaining the temperature at 22-23° C. The mixture was stirred at RT for 18 h, then for 2 h at 50° C., cooled to RT and concentrated on a rotatory evaporator at 45° C./10 mbar to give 80.6 g crude product as a yellowish oil. This material was dissolved in 161 mL dichloromethane and the solution was slowly cooled to −5° C., whereas at −2° C. crystallization occurred. The suspension was stirred between −5 and −10° C. for 30 min, then 645 ml heptane was added slowly and stirring was continued for 30 min. The crystals were filtered off, washed with 108 mL cold heptane (pre-cooled to −5° C.) and dried during 16 h at RT/10 mbar, to give 71.6 g 4-hydroxymethyl-5H-furan-2-one (87% yield; assay: 98.6%).

Example 4b

Alternative Synthesis of 4-hydroxymethyl-5H-furan-2-one

A 350 mL sulfonation flask equipped with magnetic stirring bar, thermometer, dropping funnel and an argon inlet, was charged with 58 mL dichloromethane, 43 ml de-ionized water and 26.28 g (60 mmol) ethoxycarbonylmethyltriphenylphosphonium bromide. To the clear two-phase system was added at ca. 2° C. within 15 min 35 mL (70 mmol) of 2N NaOH solution while vigorously stirring. After an additional stirring time of 15 min the phases were separated, the aqueous phase was extracted with 24 mL dichloromethane and the combined organic phases were dried over magnesium sulfate. After filtration, the obtained solution was added to a 200 ml sulfonation flask (equipped with magnetic stirring bar, thermometer and an argon inlet) which had previously been charged with 4.596 g (50 mmol) of 1,3-dihydroxyacetone. A clear yellow-orange solution formed which was stirred at RT for 22 h. The resulting clear yellow solution was vigorously stirred 4-times with 50 mL each of de-ionized water and the phases were separated each time. The combined yellow aqueous extracts were treated with 1 g of charcoal and filtered. The now colorless solution was concentrated on a rotary evaporator at 40° C./10 mbar and the residue was azeotropically dried with 50 ml toluene. The resulting pale-yellow oil was dissolved in 50 ml dichloromethane, and the solution was dried over magnesium sulfate, filtered and evaporated to provide 4.77 g of a clear pale yellow oil. This material was dissolved at RT in 15 mL dichloromethane, the solution cooled to −5° C., seeded with a few seeding crystals whereby crystallization occurred and the temperature rose to 5° C. The suspension was stirred at 5° C. for 15 min, then at −5 to −10° C. for 30 min, then slowly treated with 60 ml heptane and further stirred at −5 to −10° C. for 30 min. The crystals were filtered off, washed with 15 mL cold heptane and dried (RT/ 0.1 mbar/3 h) to provide 4.46 g 4-hydroxymethyl-5H-furan-2-one (78% yield; HPLC purity 90.4%).

Example 5

Example 5a

Preparation of 4-fluoromethyl-5H-furan-2-one

A 6 L reactor equipped with a mechanical stirrer, a Pt-100 thermometer, a dropping funnel and a nitrogen inlet was charged with 500 g (4.38 mmol) 4-hydroxymethyl-5H-furan-2-one and 2.0 L dichloromethane. The solution was cooled to −10° C. and 1.12 kg (4.82 mol) bis-(2-methoxyethyl)aminosulfur trifluoride (Deoxo-Fluor) was added during 50 min, maintaining the temperature at −5 to −10° C. with a cooling bath. During the addition a yellowish emulsion formed, which dissolved to an orange-red solution after completed addition. This solution was stirred for 1.5 h at 15-20° C., then cooled to −10° C. A solution of 250 ml water in 1.00 L ethanol was added during 30 min, maintaining the temperature between −5 and −10° C., before the mixture was allowed to reach 15-20° C. It was then concentrated in a rotary evaporator to a volume of ca. 1.6 L at 40° C./600-120 mbar. The residue was dissolved in 2.0 L dichloromethane and washed three times with 4.0 L 1N hydrochloric acid. The combined aqueous layers were extracted three times with 1.4 L dichloromethane. The combined organic layers were evaporated in a rotary evaporator to give 681 g crude product as a dark brown liquid. This material was distilled over a Vigreux column at 0.1 mbar, the product fractions being collected between 71 and 75° C. (312 g). This material was re-distilled under the same conditions, the fractions being collected between 65 and 73° C., to give 299 g 4-fluoromethyl-5H-furan-2-one (58% yield; assay: 99%).

Example 5b

Alternative Preparation of 4-fluoromethyl-5H-furan-2-one

A 250 mL sulfonation flask equipped with magnetic stirring bar, thermometer, dropping funnel and argon in/outlet was charged with 10.00 g (87.64 mmol) 4-hydroxymethyl-5H-furan-2-one, 75 mL ethyl acetate and at 0° C. (ice-ethanol bath) with 30 mL (175.3 mmol) diisopropylethyl-amine. The mixture was stirred at 0° C. for 5 min. Then 34 mL (177.9 mmol) perfluoro-1-butanesulfonyl fluoride were added within 10 min. The milky solution was allowed to attain RT whereby a clear yellow solution formed after ca. 10 min and stirred at RT for 3.5 h. The resulting black reaction mixture was evaporated on the rotary evaporator and the residue dried (RT/0.1 mbar/1 h) to provide 46.3 g of a black oil. Filtration over on 70 g silica gel with ca. 1.2 L hexane/ethyl acetate 1:1 afforded 21.8 g of yellow-brown oil which was subjected to distillation over a 10 cm Vigreux column to afford 4.37 g 4-fluoromethyl-5H-furan-2-one (b.p. 60-64° C./0.1 mbar) as yellowish oil which solidified upon seeding with a few seeding crystals (43% yield).

Example 5c

Alternative Preparation of 4-fluoromethyl-5H-furan-2-one

A 50 mL Schlenk tube equipped with rubber septum and argon in/outlet was charged with 1.03 g (9.027 mmol) 4-hydroxymethyl-5H-furan-2-one, 10 mL ethyl acetate and 9.35 mL (54.6 mmol) diisopropylethylamine. To the resulting two-layer system were added dropwise via syringes under cooling (ice bath) 3.42 g (18.07 mmol) diisopropylethylamine trishydrofluoride and then 3.45 mL (18.06 mmol) perfluoro-1-butanesulfonyl fluoride. The resulting greenish-black mixture was allowed to attain RT and stirred at RT for 2.5 h. The reaction mixture was evaporated on the rotary evaporator and the residue dried at 0.1 mbar to provide 10.0 g of a black oil. Chromatography on 50 g silica gel with hexane/ethyl acetate 1:1 afforded 0.87 g of crude product as yellow oil. A quantity of 760 mg of this oil was distilled (bulb-to-bulb, oven temperature 110° C./0.1 mbar) to afford 700 mg of 4-fluoromethyl-5H-furan-2-one as colorless oil which solidified upon standing (76% yield).

Example 5d

Alternative Preparation of 4-fluoromethyl-5H-furan-2-one 1-tert-Butoxy-3-fluoro-propan-2-ol A 1.5 L 4-necked sulfonation flask equipped with magnetic stirring bar, reflux condenser, thermometer and an argon in/outlet, was charged with 333.3 mL triethylene glycol, 235.2 g (3.012 mol) finely ground potassium hydrogendifluoride and 200 g (1.536 mol) 2-tert-butoxymethyl-oxirane. The suspension was heated under stirring at an internal temperature of 130° C. for 7.5 h. The mixture was allowed to cool to RT over night, treated with 670 mL water and 350 mL tert-butyl methyl ether, the phases were separated and the aqueous phase was extracted with 350 ml tert-butyl methyl ether. The combined organic phases were washed with 350 mL brine, dried over sodium sulfate, filtered and evaporated. The brown oily residue (286 g) was distilled to provide 141 g (61%) 1-tert-butoxy-3-fluoro-propan-2-ol as colorless liquid, b.p. 80-93° C./70-40 mbar. GC composition: 1.1% 2-tert-butoxymethyl-oxirane, 95.1% 1-tert-butoxy-3-fluoro-propan-2-ol and 3.8% of 3-tert-butoxy-2-fluoro-propan-1-ol. $^1$H-NMR (CDCl$_3$, 300 MHz): 4.45 (dxm, J$_{H,F}$=46, —CH$_2$— F); 3.93 (m, br, H—C(2); 3.45 (m, —CH$_2$—O); 2.55 (d, br, J=6, OH); 1.20 (s, C(CH$_3$)$_3$).

1-tert-Butoxy-3-fluoro-propan-2-one

A 2.5 L 4-necked sulfonation flask equipped with mechanical stirrer, dropping funnel, thermometer and an argon in/outlet, was charged with 141 g (938.8 mmol) 1-tert-butoxy-3-fluoro-propan-2-ol, 400 mL dichloromethane, 30.02 g (357.3 mmol) sodium bicarbonate, 400 mL de-ionized water and 10.68 g (89.78 mmol) potassium bromide. The two-phase system was cooled to 0° C. and 712.1 mg (4.56 mmol) 2,2,6,6-tetramethyl-1-piperidinyloxy radical (TEMPO) were added. To the resulting light orange mixture were added within 2 h 609.1 g (1.072 mol) sodium hypochlorite solution 13.1% while vigorously stirring whereupon the internal temperature transiently rose to 15° C. The reaction mixture was quenched at 0° C. with 9.71 mL (46.8 mmol) sodium bisulfite solution 38-40% leading to disappearance of the orange color. The phases were separated and the aqueous layer was extracted twice with 350 mL dichloromethane. The combined organic phases were washed with 400 mL brine, dried over sodium sulfate, filtered and evaporated to afford 130.02 g (93.5%) crude 1-tert-butoxy-3-fluoro-propan-2-one of 98.9% GC purity. $^1$H-NMR (CDCl$_3$, 300 MHz): 5.13 (d, $J_{H,F}$=48, —CH$_2$—F); 4.15 (d, J=1.5, —CH$_2$—O); 1.22 (s, C(CH$_3$)$_3$).

3-tert-Butoxymethyl-4-fluoro-3-hydroxybutyric acid tert-butyl ester

To a cold solution of 8.08 g (79.8 mmol) diisopropylamine in 50 mL tetrahydrofuran were added via syringe 50 mL butyllithium solution (1.6 M in hexane, 80 mmol) at an internal temperature of −20° C. to −10° C. The light-yellow solution was stirred at −5° C. for 15 min, then cooled to −74° C. and 9.30 g (80 mmol) tert-butyl acetate were added dropwise within 5 min at an internal temperature below −65° C. The solution was allowed to attain −20° C. within a period of 30 min, then re-cooled to −75° C. and 10.8 g (72.9 mmol) 1-tert-butoxy-3-fluoro-propan-2-one were added drop by drop at below −65° C. within 5 min. The reaction mixture was allowed to attain 0° C., treated with 80 mL sat. ammonium chloride solution and the phases were separated. The organic layer was washed successively with 80 mL 5 M ammonium chloride solution, 80 mL 5% sodium bicarbonate solution and 40 mL brine, dried over magnesium sulfate, filtered and evaporated to provide 19.64 g slightly yellow oil containing by GC analysis 97.2% of 3-tert-butoxymethyl-4-fluoro-3-hydroxybutyric acid tert-butyl ester; 102% yield weight/weight; 99% assay-corrected yield. $^1$H-NMR (CDCl$_3$, 300 MHz): 4.38 (dxm, $J_{H,F}$=47, —CH$_2$—F); 3.87 (s, OH); 3.37 (d, J=2.3, —CH$_2$—O); 2.54 (m, —CH$_2$—C(O); 1.47 (s, C(O)O—C(CH$_3$)$_3$); 1.18 (O—C(CH$_3$)$_3$).

4-Fluoromethyl-4-hydroxy-dihydro-furan-2-one

A solution of 17.47 g crude 3-tert-butoxymethyl-4-fluoro-3-hydroxybutyric acid tert-butyl ester (from 64.85 mmol 1-tert-butoxy-3-fluoro-propan-2-one) in 20 mL trifluoroacetic acid was stirred at 40° C. for 30 min. The resulting brown solution was evaporated and the residue subjected to bulb-to-bulb distillation at 150-160° C./0.4 mbar to provide 8.40 g (96.6% from 1-tert-butoxy-3-fluoro-propan-2-one) 4-fluoromethyl-4-hydroxy-dihydro-furan-2-one as yellow oil. $^1$H-NMR (CDCl$_3$, 300 MHz): 4.46 (d, J=47, CH$_2$F); 4.33 (AB with fine structure, J=10 and 2, —CH$_2$—O); 3.33 (s br, OH); 2.70 (AB with fine structure, J=18, —CH$_2$—C(O)).

Alternative Preparation of 4-fluoromethyl-4-hydroxy-dihydro-furan-2-one: One-Pot Procedure without Isolation of 3-tert-butoxymethyl-4-fluoro-3-hydroxybutyric acid tert-butyl ester A 750 mL 4-necked sulfonation flask equipped with magnetic stirring bar, thermometer and an argon in/outlet, was charged with 16.87 g (166.7 mmol) diisopropylamine and 100 mL tetrahydrofuran. The solution was cooled to −74° C. and 100 mL butyllithium 1.6M in hexane were added leading to a raise of the internal temperature to −55° C. The light-yellow solution was stirred at −50° C. to −10° C. for 30 min (ice/ethanol cooling bath), then re-cooled to −74° C. and 19.36 g (166.7 mmol) tert-butyl acetate were added dropwise. The slightly turbid solution was stirred at −20° C. for 30 min, then re-cooled to −74° C. and 22.23 g (150 mmol) crude 1-tert-butoxy-3-fluoro-propan-2-one were added dropwise within 15 min. The acetone/CO$_2$ bath was replaced by an ice/water bath and the reaction mixture was stirred at ca. −10° C. for 45 min. After re-cooling to −75° C. 52.5 g (508.5 mmol) sulfuric acid 95% were added drop by drop within 15 min. The resulting two-phase mixture was allowed to attain RT (45 min) and then heated under reflux for 2 h (oil bath temperature 80° C., internal temperature 54-61° C., strong gas evolution). After cooling to RT the mixture was treated with sodium chloride solution 10% (50 mL), the phases were separated and the aqueous layer was extracted with ethyl acetate (5×150 mL). The combined organic phases were washed with sat. sodium bicarbonate solution (2×50 mL) and brine (2×50 mL), dried over magnesium sulfate, filtered and evaporated (40° C./15 mbar) to provide 15.78 g of crude 4-fluoromethyl-4-hydroxy-dihydro-furan-2-one as yellow-brown oil. This material contained 2% acetic acid by $^1$H-NMR. From the combined aqueous layers an additional 1.38 g of crude 4-fluoromethyl-4-hydroxy-dihydro-furan-2-one were obtained by further extraction with ethyl acetate (2×150 mL) followed by further work-up as described above; combined yield 17.16 g (85.3%) of crude 4-fluoromethyl-4-hydroxy-dihydro-furan-2-one.

$^1$H-NMR (CDCl$_3$, 300 MHz): 4.47 (d, J=47, CH$_2$F); 4.31 (AB with fine structure, J=10 and 2, —CH$_2$—O); 2.84 (s br, OH); 2.69 (AB with fine structure, J=18, —CH$_2$—C(O)).

4-Fluoromethyl-5H-furan-2-one

A 350 mL 4-necked sulfonation flask equipped with magnetic stirring bar, dropping funnel, thermometer and an argon in/outlet, was charged with 16.76 g (125 mmol) crude 4-fluoromethyl-4-hydroxy-dihydro-furan-2-one and 100 mL dichloromethane. At 0-3° C. 14.18 mL acetic anhydride (150 mmol) and 19.26 mL (138.2 mmol) triethylamine were added dropwise within 5 and within 10 min. Then 311.7 mg (2.55 mmol) 4-dimethylaminopyridine were added as solid and the ice bath was removed. The internal reaction temperature rose to 27° C. and the reaction solution turned brownish-black. After stirring at RT for 3.5 h the solution was cooled to 0° C., quenched with 23 mL ethanol, stirred at RT for 1 h and diluted with 50 mL dichloromethane. The solution was washed with 1N HCl solution saturated with sodium chloride (70 mL, ca. 30 g sodium chloride/100 mL 1N HCl) and with brine (3×35 mL), dried over magnesium sulfate and filtered. The dark yellow-brown solution was further washed with brine (2×35 mL), dried over magnesium sulfate, filtered and evaporated to provide 13.07 g dark yellow-brown oil. An additional 2.05 g of dark yellow-brown oil was obtained from the combined aqueous phases by extraction with dichloromethane (2×50 mL) followed by washing the combined extracts with brine, drying over magnesium sulfate, filtration and evaporation; combined yield 15.12 g. Of this material 14.87 g were subjected to bulb-to-bulb distillation at ca. 110° C./0.3 mbar to afford 12.6 g (86.8%) of 4-fluoromethyl-5H-furan-2-one as light-yellow oil. Crystallization from 45 mL tert-butyl methyl ether at −20° C. over night afforded, after filtration, washing with 10 mL cold tert-butyl methyl ether and drying (RT/0.1 mbar/5 h) 8.97 g (61.8%) of 4-fluoromethyl-5H-furan-2-one as white, low-melting crystals. An additional 1.53 g of white, crystalline 4-fluoromethyl-5H-furan-2-one were obtained from the mother liquor by concentration to 13 g and storing over night at −20° C.; combined yield 10.50 g (72.4%).

$^1$H-NMR (CDCl$_3$, 300 MHz): 6.11 (s with fine structure, H—C(3); 5.33 (d with fine structure, $J_{H,F}$=46, —CH$_2$F); 4.89 (s with fine structure, —CH$_2$—O).

Example 5e

Alternative Preparation of 4-fluoromethyl-5H-furan-2-one

4-Fluoromethyl-4-hydroxy-dihydro-furan-2-one

A solution of 20.00 g (75.67 mmol) 3-tert-butoxymethyl-4-fluoro-3-hydroxy-butyric acid tert-butyl ester (as prepared in Example 5d, step (ii)) in 15.1 ml 1,2-dimethoxyethane was treated with 200 mg (1.94 mmol) sulfuric acid 95% and the mixture was heated with stirring under reflux conditions for 2.75 h. The dark-brown solution was treated at RT with 1.03 g (7.57 mmol) sodium acetate trihydrate and the mixture stirred for 30 min. Ethyl acetate (15 ml) and magnesium sulfate (4.7 g) were added, and the mixture was filtered. The filtrate was evaporated (15 mbar/40° C.) to provide 10.24 g of dark-brown oil. Distillation (bulb to bulb, b.p. ca. 150° C./0.1 mbar) afforded 9.28 g (91%) 4-fluoromethyl-4-hydroxy-dihydro-furan-2-one as yellow oil.

An analogous reaction of 26.4 g (100 mmol) 3-tert-butoxymethyl-4-fluoro-3-hydroxybutyric acid tert-butyl ester in 20 ml 1,4-dioxane provided, after distillation, 12.52 g (93%) of 4-fluoromethyl-4-hydroxy-dihydro-furan-2-one as yellow oil.

4-Fluoromethyl-5H-furan-2-one

To a solution of 20.5 g (152.9 mmol) of crude 4-fluoromethyl-4-hydroxy-dihydro-furan-2-one in 350 ml dichloromethane were added at −15° C. 22.0 ml (303 mmol) thionyl chloride and subsequently, within 15 min, 49 ml pyridine. The temperature rose to 0° C. The brown solution was allowed to attain RT, and stirred for 4 h. GC analysis showed <3% of starting material left. The red-brown solution was transferred into a separatory funnel with the aid of 100 ml dichloromethane and the solution was washed with 1N hydrochloric acid in saturated sodium chloride solution (2×100 ml and 1×50 ml) which led to an exothermic reaction and gas evolution. The organic phase was further washed with saturated sodium chloride solution (2×100 ml), dried over sodium sulfate, filtered and evaporated to provide 14.49 g of brown oil. Distillation (bulb to bulb, oven temp. ca. 130° C., 0.2 mbar) afforded 13.58 g of yellow oil. This material was dissolved in 20 ml tert-butyl methyl ether and the solution was stored in a freezer at −20° C. for 24 h. The crystals formed were collected by filtration, washed with 10 ml cold tert-butyl methyl ether and dried (rt/0.1 mbar/2 h) to furnish 11.96 g (67%) of 4-fluoromethyl-5H-furan-2-one as off-white crystalline powder.

Example 5f

Alternative Preparation of 4-fluoromethyl-5H-furan-2-one

To 76.80 g (290.5 mmol) 3-tert-butoxymethyl-4-fluoro-3-hydroxybutyric acid tert-butyl ester were added at 3° C. 170.4 g (1.464 mol) trifluoroacetic acid under stirring within 12 min. The solution was stirred at 3° C. for 10 min, then at RT for 4.5 h. The resulting pale brown clear solution was evaporated (15 mbar/40° C.) to provide 49.37 g of dark-brown oil containing the intermediate 4-fluoromethyl-4-hydroxy-dihydro-furan-2-one. To this material were added 45.23 ml (478.5 mmol) acetic anhydride and the solution was rolled on a rotary evaporator at a water-bath temperature of 60° C. for 2 h. After standing over night, the dark-brown solution was evaporated (60° C./3 mbar) to afford 53.5 g of dark-brown oil, which by $^1$H-NMR consisted of the intermediate 4-acetoxy-4-fluoromethyl-dihydro-furan-2-one and of residual acetic acid.

To a mixture of this material in 200 ml de-ionized water were added in one portion 207.6 g (2.506 mol) sodium acetate and the red-brown suspension was stirred at 50° C. for 4.5 h. The resulting red-brown, slightly turbid solution was transferred into a separatory funnel and extracted with dichloromethane (6×100 ml). After the $2^{nd}$, $3^{rd}$, $4^{th}$ and $5^{th}$ extraction were added each time 50 ml 10% NaCl solution to assist in the breaking of emulsions. The combined dichloromethane extracts were dried over magnesium sulfate, filtered and evaporated (40° C./15 mbar) to provide 28.12 g of yellow-brownish oil. Distillation afforded 25.49 g of 4-fluoromethyl-5H-furan-2-one as colorless liquid, b.p. ca. 80° C./0.1 mbar. The distillate was dissolved in 25 ml tert-butyl methyl ether and the clear colorless solution was stored at −20° C. over night. The precipitate was isolated by filtration, washed with 20 ml cold tert-butyl methyl ether and dried (0.1 mbar/rt/2.5 h) to provide 22.27 g (66% based on 3-tert-butoxymethyl-4-fluoro-3-hydroxybutyric acid tert-butyl ester) of 4-fluoromethyl-5H-furan-2-one as white crystalline powder, m.p. ca. 30-40° C.

Example 6

Preparation of (S)-4-fluoromethyl-dihydro-furan-2-one

Example 6.1

In-Situ Preparation of the Catalyst Solution

In a glove box (O$_2$ content<2 ppm) an Erlenmeyer flask was charged with 21.2 mg [Rh(COD)Cl]$_2$ (4.31×10−5 mol), 55.9 mg (S)-(+)-TMBTP (9.47×10−5 mol) and 40 mL dichloromethane. The mixture was stirred 15 min at room temperature.

Asymmetric Hydrogenation (S/C 500)

In the glove box the above catalyst solution was added to 5.0 g (43.1 mmol) 4-fluoro-methyl-5H-furan-2-one previously placed into a 185 mL autoclave. The autoclave was sealed and pressurized with hydrogen (50 bar). The reaction mixture was hydrogenated 18 h at 40° C. under stirring. At this point the reaction was complete according to GC analysis. The hydrogenation mixture, an orange solution, was removed from the autoclave and concentrated in vacuo. The residue was distilled at 0.05 mbar and 50-52° C. to afford 4.8 g (94%) (S)-4-fluoromethyl-dihydro-furan-2-one. The chemical purity of the product was 99.3% (GC-area) and the enantiomeric ratio (S)/(R) 96.3:3.7. The chemical purity of the product was determined using a Hewlett Packard GC Mod. 6890N with a Machery-Nagel Optima-1 column (25 m×0.32 mm). The enantiomeric ratio of the product was determined by GC on a BGB-175 (30 m×0.25 mm; BGB-Analytik AG) gamma-cyclodextrin based column.

Example 6.2

An experiment was carried out in analogy to the experiment described in example 6.1 using 1.0 g (8.61 mmol) 4-fluoromethyl-5H-furan-2-one as the substrate with an increased substrate/catalyst ratio of S/C 1000. 2.12 mg [Rh(COD)Cl]$_2$ (4.31×10$^{-6}$ mol), 5.6 mg (S)-(+)-TMBTP (9.47×10$^{-6}$ mol) and 8 mL dichloromethane as the solvent were used. After distillation 1.0 g (98%) (S)-4-fluoromethyl-dihydro-furan-2-one was obtained. The chemical purity of the product was 99.0% (GC-area) and the enantiomeric ratio (S)/(R) 96.4:3.6; [α]$_D$–41.4 (c=1, CH$_2$Cl$_2$).

Example 6.3

In-Situ Preparation of the Catalyst Solution

In a glove box (O$_2$ content<2 ppm) an Erlenmeyer flask was charged with 1.59 mg [Rh(COD)Cl]$_2$ (3.23×10–6 mol), 4.2 mg (S)-(+)-TMBTP (7.11×10–6 mol) and 1 mL dichloromethane. The mixture was stirred 15 min at room temperature.

Asymmetric Hydrogenation

In the glove box the above catalyst solution was added in a vial to 75 mg (6.46×10–6 mol) 4-fluoromethyl-5H-furan-2-one and the vial was placed into an autoclave. The autoclave was sealed and pressurized with hydrogen (50 bar). The reaction mixture was hydrogenated 18 h at 40° C. under stirring. The hydrogenation mixture was removed from the autoclave and passed through a small silica gel column to remove most of the catalyst. The product was collected and analyzed by GC as described in example 6.1. The conversion was found to be 100% and the enantiomeric ratio of the product (S)/(R) 95.9:4.1

Examples 6.4-6.19

The experiments in Table 1 have been carried out in analogy to example 6.3 using various chiral diphosphines for the in-situ formation of the catalyst with [Rh(COD)Cl]$_2$.

TABLE 1

| Exp. No. | Diphosphine | S/C | Conv. % | er (S)/(R) |
|---|---|---|---|---|
| 6.4 | (R)-(S)-NMe$_2$-PPh$_2$-Mandyphos | 100 | 100 | 15.2:84.8 |
| 6.5 | (R)-(S)-Walphos | 100 | 100 | 17.5:82.5 |
| 6.6 | (S)-BINAP | 100 | 100 | 79.6:20.4 |
| 6.7 [a] | (S)-BINAP | 100 | 100 | 81.6:18.4 |
| 6.8 [b] | (S)-BINAP | 200 | 100 | 80.2:19.8 |
| 6.9 | (S)-MeOBIPHEP | 100 | 100 | 77.3:22.7 |
| 6.10 [a] | (S)-MeOBIPHEP | 100 | 100 | 78.8:21.2 |
| 6.11 | (S)-BIPHEMP | 100 | 100 | 76.2:23.8 |
| 6.12 [a] | (S)-BIPHEMP | 100 | 100 | 78.5:21.5 |
| 6.13 | (S)-Synphos | 100 | 100 | 77.8:22.2 |
| 6.14 | (S)-Solphos | 100 | 100 | 76.9:23.1 |
| 6.15 | (S)-(3-Thienyl)-MeOBIPHEP | 100 | 100 | 73.4:26.6 |

TABLE 1-continued

| Exp. No. | Diphosphine | S/C | Conv. % | er (S)/(R) |
|---|---|---|---|---|
| 6.16 | (S)-3,5-tBu-MeOBIPHEP | 100 | 100 | 71.7:28.3 |
| 6.17 [a] | (S)-3,5-tBu-MeOBIPHEP | 100 | 100 | 73.0:27.0 |
| 6.18 | (S)-3,5-Xyl-MeOBIPHEP | 100 | 100 | 72.6:27.4 |
| 6.19 | (R,R)-DIOP | 100 | 100 | 22.4:77.6 | solvent = Ph-CF$_3$
1 g-scale reaction

Example 6.20

In a glove box (O$_2$ content<2 ppm) 9.81 mg Ru(OAc)$_2$((R)-3,5-iPr-MeOBIPHEP) (8.61×10–6 mol) was added in a vial to 100 mg 4-fluoromethyl-5H-furan-2-one (8.61×10–4 mol) followed by 1 mL dichloromethane. The vial was placed into an autoclave and the autoclave was sealed and pressurized with hydrogen (50 bar). The reaction mixture was hydrogenated 18 h at 40° C. under stirring. The hydrogenation mixture was removed from the autoclave and concentrated in vacuo. The residue was distilled (bulb-to-bulb) and analyzed by GC as described in example 6.1. The conversion was found to be 100% and the enantiomeric ratio of the product (S)/(R) 95.2:4.8.

Examples 6.21-6.34

The experiments in Table 2 have been carried in analogy to example 6.20 using various chiral ruthenium catalysts and dichloromethane as the solvent (unless otherwise stated). The product was separated from the catalyst either by distillation or by chromatography on a small silica gel column.

TABLE 2

| Exp. | Chiral Ruthenium Catalyst | S/C | % Conv. | er (S)/(R) |
|---|---|---|---|---|
| 6.21 | Ru(OAc)$_2$((R)-3,5-tBu-MeOBIPHEP) | 100 | 100 | 95.0:5.0 |
| 6.22 | Ru(OAc)$_2$((R)-3,5-Xyl-MeOBIPHEP) | 100 | 100 | 90.9:9.1 |
| 6.23 [a] | RuCl$_2$((R)-3,5-Xyl-MeOBIPHEP)((S-DAIPEN) | 10 | 100 | 90.6:9.4 |
| 6.24 | Ru(OAc)$_2$((R)-BIPHEMP) | 50 | 100 | 90.5:9.5 |
| 6.25 | Ru(OAc)$_2$((R)-p-Tol-BINAP) | 50 | 100 | 89.5:10.5 |
| 6.26 | Ru(OAc)$_2$((R)-BINAP) | 100 | 100 | 89.0:11.0 |
| 6.27 | Ru(OAc)$_2$((R)-MeOBIPHEP) | 100 | 100 | 88.9:11.1 |
| 6.28 | Ru(OAc)$_2$((R)-DiMeOBIPHEP) | 100 | 100 | 87.6:12.4 |
| 6.29 | Ru(OAc)$_2$((R)-BIPHOMP) | 100 | 100 | 85.9:14.1 |
| 6.30 | Ru(PhCOO)$_2$((R)-MeOBIPHEP) | 100 | 100 | 83.0:17.0 |
| 6.31 | Ru(OAc)$_2$((R)-BIBFUP) | 50 | 100 | 81.4:18.5 |
| 6.32 [b] | RuH(BH$_4$)((R)-3,5-Xyl-MeOBIPHEP)((R,R-DPEN) | 10 | 100 | 25.7:74.3 |
| 6.33 | Ru(OAc)$_2$((S)-3,5-tBu, 4-MeO-BIPHEP) | 100 | 100 | 10.2:89.8 |
| 6.34 | Ru(OAc)$_2$((S)-3,5-iPr, 4-MeO-MeOBIPHEP) | 100 | 100 | 5.3:94.7 |

Conditions used: 75 mg substrate in 1 mL isopropanol+t-BuONa (3.1 mg) as an additive, 10 bar H$_2$ Conditions used: 75 mg substrate in 1 mL isopropanol, 10 bar $H_2$

Example 6.35

In a glove box ($O_2$ content<2 ppm) 10.77 mg $Ru(OAc)_2$ ((R)-3,5-tBu-MeOBIPHEP) (8.61×10−6 mol) was added in a vial to 100 mg 4-fluoromethyl-5H-furan-2-one (8.61×10−4 mol) followed by 1 mL methanol. The vial was placed into an autoclave and the autoclave was sealed and pressurized with hydrogen (50 bar). The reaction mixture was hydrogenated 18 h at 40° C. under stirring. The hydrogenation mixture was removed from the autoclave and concentrated in vacuo. The residue was distilled (bulb-to-bulb) and analyzed by GC as described in example 6.1. The conversion was found to be 100% and the enantiomeric ratio of the product (S)/(R) 96.2:3.8.

Examples 6.36-6.41

The experiments in Table 3 have been carried in analogy to example 6.35 using various chiral ruthenium catalysts and methanol as the solvent

TABLE 3

| Exp. | Chiral Ruthenium Catalyst | S/C | % Conv. | er (S)/(R) |
|---|---|---|---|---|
| 6.36 | $Ru(OAc)_2$((R)-3,5-iPr-MeOBIPHEP) | 100 | 100 | 95.7:4.3 |
| 6.37 | $Ru(OAc)_2$((R)-3,5-Xyl-MeOBIPHEP) | 100 | 100 | 90.6:9.4 |
| 6.38 | $Ru(OAc)_2$((R)-BINAP) | 100 | 100 | 88.4:11.6 |
| 6.39 | $Ru(OAc)_2$((R)-MeOBIPHEP) | 100 | 100 | 84.2:15.8 |
| 6.40 | $Ru(OAc)_2$((S)-3,5-tBu, 4-MeO-MeOBIPHEP) | 100 | 100 | 6.6:93.4 |
| 6.41 | $Ru(OAc)_2$((S)-3,5-iPr, 4-MeO-MeOBIPHEP) | 100 | 100 | 4.2:95.8 |

Example 6.42

In a glove box ($O_2$ content<2 ppm) 10.77 mg $Ru(OAc)_2$ ((R)-3,5-tBu-MeOBIPHEP) (8.61×10−6 mol) (S/C 1000) was added in a vial to 1.0 g 4-fluoromethyl-5H-furan-2-one (8.61×10−3 mol) followed by 4 mL 2,2,2-trifluoroethanol. The vial was placed into an autoclave (35 mL) and the autoclave was sealed and pressurized with hydrogen (50 bar). The reaction mixture was hydrogenated 18 h at 40° C. under stirring. The hydrogenation mixture was removed from the autoclave and concentrated in vacuo. The residue was distilled (bulb-to-bulb) and analyzed by GC as described in example 6.1. The conversion was found to be 100% and the enantiomeric ratio of the product (S)/(R) 99.7:0.3.

Example 6.43 g 4-fluoromethyl-5H-furan-2-one (8.61×10−3 mol) was hydrogenated in the presence of 10.77 mg $Ru(OAc)_2$((R)-3, 5-tBu-MeOBIPHEP) (8.61×10−6 mol) (S/C 1000) as described in example 6.42, however using 4 mL ethanol as the solvent in place of 2,2,2-trifluoroethanol. The conversion was found to be 100% and the enantiomeric ratio of the product (S)/(R) 96.3:3.7.

Example 6.44 g 4-fluoromethyl-5H-furan-2-one (8.61×10−3 mol) was hydrogenated in the presence of 10.77 mg $Ru(OAc)_2$((R)-3, 5-tBu-MeOBIPHEP) (8.61×10−6 mol) (S/C 1000) as described in example 6.42, however using 4 mL n-propanol as the solvent in place of 2,2,2-trifluoroethanol. The conversion was found to be 100% and the enantiomeric ratio of the product (S)/(R) 96.5:3.5.

Example 6.45

In a glove box ($O_2$ content<2 ppm) a 185 mL autoclave equipped with a glass vial and a mechanical stirrer was charged with 4.0 g 4-fluoromethyl-5H-furan-2-one (3.45× 10−2 mol) and 14.36 mg $Ru(OAc)_2$((R)-3,5-tBu-MeOBIPHEP) (1.15×10−5 mol) (S/C 3000). The components were dissolved in 14 mL methanol. The autoclave was sealed and pressurized with hydrogen (50 bar). The reaction mixture was hydrogenated 20 h at 40° C. under stirring. At this point the reaction was complete according to GC analysis. The hydrogenation mixture was removed from the autoclave and concentrated in vacuo. The residue was distilled (bulb-to-bulb) to afford 3.99 g (98%) (S)-4-fluoromethyl-dihydro-furan-2-one, $^1$H NMR (400 MHz, $CDCl_3$) δ 2.41 (dd, J=17.9, 6.4 Hz, 1H), 2.67 (ddd, J=17.8, 9.2, 0.8 Hz, 1H), 2.88-3.04 (m, 1H), 4.22 (dd, J=9.4, 5.6 Hz, 1H), 4.37-4.44 (m, 1H), 4.44 (ddd, J=9.3, 7.8 1.2 Hz, 1H), 4.52 (ddd, J=11.9, 9.5, 5.8 Hz, 1H) ppm; 2J (H-6, F)=46.7 Hz. The chemical purity of the product was 99.5% by GC-area as determined using a Hewlett Packard GC Mod. 6890N with a Machery-Nagel Optima-1 column (25 m×0.32 mm). The enantiomeric ratio of the product was determined by GC on a BGB-175 (30 m×0.25 mm; BGB-Analytik AG) gamma-cyclodextrin based column to be (S)/(R) 97.0:3.0.

Example 6.46

A 2 L autoclave equipped with a mechanical stirrer was charged with a solution of 96.0 g 4-fluoromethyl-5H-furan-2-one (8.27×10−1 mol) in 284 mL methanol. The autoclave was sealed and pressurized several times with argon (7 bar) in order to remove any traces of oxygen. At ~1 bar argon, a solution of 82.74 mg $Ru(OAc)_2$((R)-3,5-tBu-MeOBIPHEP) (6.62×10−5 mol) (S/C 12500) in 100 mL methanol was added under stirring from a catalyst addition device previously charged in a glove box ($O_2$ content<2 ppm) and pressurized with argon (7 bar). The argon atmosphere in the autoclave was replaced by hydrogen (5 bar). At this pressure, the reaction mixture was stirred (~800 rpm) for 20 h at 30° C. and then removed from the autoclave and concentrated in vacuo. The residue was distilled to afford 91.8 g (94%) (S)-4-fluoromethyl-dihydro-furan-2-one. The chemical purity of the product was 99.7% by GC-area, and the enantiomeric ratio of the product was determined to be (S)/(R) 97.7:2.3.

Example 7

Preparation of (R)-4-chloro-3-fluoromethyl-butyryl chloride

A 350 mL reactor equipped with a mechanical stirrer, a Pt-100 thermometer and an argon inlet was charged with 226 g (1.90 mol) (S)-4-fluoromethyl-dihydro-furan-2-one, 64.9 g (476 mmol) zinc chloride and 698 ml (9.52 mol) thionyl chloride. The mixture was refluxed for 66 h, then allowed to cool to RT. The white precipitate, which already formed during the reaction, was filtered off under an argon atmosphere and washed with a small amount of thionyl chloride. The filtrate was distilled as follows: Thionyl chloride was collected as a first fraction at 30° C. oil bath temperature/20 mbar. Then the oil bath temperature was slowly increased and the fractions between 57 and 62° C./1 mbar were collected, to give 196 g (R)-4-chloro-3-fluoromethyl-butyryl chloride (58% yield; assay: 97%).

Example 8

Preparation of (2S,3S,11bS)-3-((4S)-Fluoromethyl-2-oxo-pyrrolidin-1-yl)-9,10-dimethoxy-1,3,4,6,7,11b-hexahydro-2H-pyrido[2,1-a]isoquinolin-2-yl]-carbamic acid tert-butyl ester A 4.5 L reactor equipped with a mechanical stirrer, a Pt-100 thermometer, a dropping funnel and a nitrogen inlet was charged with 160 g (419 mmol) (2S,3S,11bS)-3-(3-amino-9,10-dimethoxy-1,3,4,6,7,11b-hexahydro-2H-pyrido [2,1-a]isoquinolin-2-yl)-carbamic acid tert-butyl ester 1.50 L dry THF and 29.3 mL (209 mmol) triethylamine. The suspension was cooled to 0-5° C. and a solution of 97.4 g (544 mmol) (R)-4-chloro-3-fluoromethyl-butyryl chloride in 417 mL dry THF was added during 90 min, maintaining the temperature at 0-5° C. After the addition of about half of the acid chloride solution, the reaction mixture became thick, but still remained stirrable. The mixture was stirred for 1.5 h at 0-5° C., another portion of 9.37 g (52.7 mmol) acid chloride in 35 mL dry THF was added and the mixture was stirred for another 30 min at 0-5° C. A suspension of 145 g (1.26 mol) potassium tert.-butylate in 900 mL dry THF was added during 35 min, maintaining the temperature at below 6° C. After completed addition the mixture was stirred overnight at 0° C., poured on 6.2 L half saturated brine and extracted with 6.2 L ethyl acetate. The organic layer was washed with 3.2 L half saturated brine, and the combined aqueous phases were extracted twice with 2.2 L ethyl acetate. The combined organic layers were filtered over a pad of 800 g sodium sulfate, concentrated on a rotatory evaporator at 45° C./10 mbar and dried at 40° C./0.1 mbar for 16 h, to give 225 g crude product. This material was chromatographed over silica gel with dichloromethane/THF 3:1 as eluent, to give 168 g product. This material was suspended in 800 mL methanol, heated to reflux and after 15 min allowed to slowly reach RT, resulting in a thick, but well stirrable suspension. After 4 h at RT, the reddish brown mixture was stirred at 0° C. overnight, followed by −15 to −20° C. during 2 h. The crystals were filtered off, washed portionwise with totally 250 mL cold TBME (pre-cooled to −15° C.) and dried for 6 h at 45° C./9 mbar, followed by 15 h at 45° C./0.1 mbar, to give 127 g lactam (64% yield; assay: 100%)

Example 9

Preparation of (2S,3S,11bS)-3-(3-Fluoromethyl-4-hydroxy-butyrylamino)-9,10-dimethoxy-1,3,4,6,7,11b-hexahydro-2H-pyrido[2,1-a]isoquinolin-2-yl]-carbamic acid tert-butyl ester A 1.5 L reactor equipped with a mechanical stirrer, a Pt-100 thermometer, a dropping funnel and a nitrogen inlet was charged with 50 g (128 mmol) (2S,3S,11bS)-3-amino-9,10-dimethoxy-1,3,4,6,7,11b-hexahydro-2H-pyrido[2,1-a]isoquinolin-2-yl)-carbamic acid tert-butyl ester, 500 mL toluene and 2.51 g (25.6 mmol) 2-hydroxypyridine. To this slightly brownish suspension, 22.7 g (192 mmol) of (S)-4-fluoromethyl-dihydro-furan-2-one was added dropwise at RT. No exothermy was observed during the addition. The dropping funnel was rinsed portionwise with totally 100 mL toluene. The suspension was heated to reflux, whereas it turned into a clear solution starting from 60° C., after 40 min under reflux a suspension formed again. After totally 23 h under reflux, the thick suspension was cooled to RT, diluted with 100 mL dichloromethane and stirred for 30 min at RT. After filtration, the filter cake was washed portionwise with totally 200 mL toluene, then portionwise with totally 100 mL dichloromethane. The filter cake was dried at 50° C./10 mbar for 20 h, to give 60.0 g product (94% yield; assay: 100%).

Example 10

Preparation of (2S,3S,11bS)-3-((4S)-Fluoromethyl-2-oxo-pyrrolidin-1-yl)-9,10-dimethoxy-1,3,4,6,7,11b-hexahydro-2H-pyrido[2,1-a]isoquinolin-2-yl]-carbamic acid tert-butyl ester A 1.5 L reactor equipped with a mechanical stirrer, a Pt-100 thermometer, a dropping funnel, a cooling bath and a nitrogen inlet was charged with 28 g (56.5 mmol) of (2S,3S,11bS)-3-(3-fluoromethyl-4-hydroxy-butyrylamino)-9,10-dimethoxy-1,3,4,6,7,11b-hexahydro-2H-pyrido[2,1-a]isoquinolin-2-yl]-carbamic acid tert-butyl ester and 750 mL THF. The mixture was cooled to 0° C. and a solution of 6.17 mL (79 mmol) methanesulfonyl chloride in 42 mL THF was added during 10 min, maintaining the temperature at 0-5° C. At 0° C. a solution of 12.6 mL (90.2 mmol) triethylamine in 42 mL THF was added during 15 min. The resulting suspension was stirred for 80 min at 0-5° C., whereas it became gradually thicker. Then 141 mL (141 mmol) 1 M lithium-bis (trimethylsilyl)amide were added to the mixture during 15 min, whereas the suspension dissolved. The solution was allowed to reach RT during 60 min under stirring. 500 mL water was added without cooling, the mixture was extracted and the aqueous phase was subsequently extracted with 500 mL and 250 mL dichloromethane. The organic layers were each washed with 300 mL half saturated brine, combined and evaporated on a rotatory evaporator. The resulting foam was dissolved in 155 mL dichloromethane, filtered and again evaporated to give 30.5 g crude product as a slightly brownish foam. This material was dissolved in 122 mL methanol, resulting in a thick suspension, which dissolved on heating to reflux. After 20 min of reflux the solution was allowed to gradually cool to RT during 2 h, whereas crystallization started after 10 min. After 2 h the suspension was cooled to 0° C. for 1 h, followed by −25° C. for 1 h. The crystals were filtered off via a pre-cooled glass sinter funnel, washed portionwise with 78 mL TBME and dried for 18 h at 45° C./20 mbar, to give 21.0 g product as white crystals (77% yield; assay: 99.5%).

Example 11

Preparation of (R)-4-bromo-3-fluoromethyl-butyric acid ethyl ester

A 250 mL round bottom flask equipped with a condenser was charged with 3.22 g (27.3 mmol) (S)-4-fluoromethyl-dihydro-furan-2-one. 16 mL (91 mmol) hydrobromic acid (33% in acetic acid) was added in one portion and the mixture was stirred at 60° C. for 45 minutes. A second portion of 16 mL (91 mmol) hydrobromic acid (33% in acetic acid) was added and stirring was continued at the same temperature for an additional 45 minutes, whereupon 96 mL ethanol were added. The resulting mixture was stirred at 60° C. for 65 minutes. The solvent was evaporated under reduced pressure (90 mbar) and the residue was dissolved in 300 mL toluene. The organic solution was washed with 300 mL saturated aqueous $NaHCO_3$ and 300 mL water. Following drying over $Na_2SO_4$, filtration and evaporation of the solvent, the crude mixture was distilled under reduced pressure (82° C./1 mbar) to give 3.96 g product (64%; assay 98.9%).

Example 12

Preparation of (2S,3S,11bS)-3-((4S)-Fluoromethyl-2-oxo-pyrrolidin-1-yl)-9,10-dimethoxy-1,3,4,6,7,11b-hexahydro-2H-pyrido[2,1-a]isoquinolin-2-yl]-carbamic acid tert-butyl ester A 25 mL round bottom flask equipped with a condenser was charged with 3.00 (7.95 mmol) (3-amino-9,10-dimethoxy-1,3,4,6,7,11b-hexahydro-2H-pyrido[2,1-a]isoquinolin-2-yl)-carbamic acid tert-butyl ester. 15 mL di-n-butyl ether was added followed by 1.98 g (8.74 mmol) (R)-4-bromo-3-fluoromethyl-butyric acid ethyl ester and 2.44 g (15.9 mmol) cesium fluoride. The heterogeneous mixture was refluxed under argon and mechanical stirring for 7.5 hours. An additional 0.36 g (1.59 mmol) (R)-4-bromo-3-fluoromethyl-butyric acid ethyl ester was added and the mixture was refluxed for 16.5 hours. The reaction mixture was allowed to cool to ambient temperature and was diluted with 25 mL dichloromethane. The organic phase was washed with saturated aqueous $NaHCO_3$ and brine and then concentrated to dryness under reduced pressure (45° C.). The solid residue was recrystallized from methanol to give 1.62 g product as beige crystals (43%, assay 92.3%). The mother liquor was concentrated to dryness and purified by chromatography over silica gel eluting with ethyl acetate/ethanol 93:7 to give an additional 0.85 g product (22%, assay 99.6%).

Example 13

Preparation of (2S,3S,11bS)-1-(2-amino-9,10-dimethoxy-1,3,4,6,7,11b-hexahydro-2H-pyrido[2,1-a]isoquinolin-3-yl)-4(S)-fluoromethyl-pyrrolidin-2-one dihydrochloride A 2.5 L reactor equipped with a mechanical stirrer, a Pt-100 thermometer, a dropping funnel and a nitrogen inlet was charged with 619 g (1.30 mol) of (2S,3S,11bS)-3-((4S)-fluoromethyl-2-oxo-pyrrolidin-1-yl)-9,10-dimethoxy-1,3,4,6,7,11b-hexahydro-2H-pyrido[2,1-a]isoquinolin-2-yl]-carbamic acid tert-butyl ester, 4.2 L isopropanol and 62 mL water and the suspension was heated to 40-45° C. In a second vessel, 1.98 L isopropanol was cooled to 0° C. and 461 mL (6.50 mol) acetyl chloride was added during 35 min, maintaining the temperature at 0-7° C. After completed addition, the mixture was allowed to reach ca. 15° C. and was then slowly added to the first vessel during 1.5 h. After completed addition the mixture was stirred for 18 h at 40-45° C., whereas crystallization started after 1 h. The white suspension was cooled to 20° C. during 2 h, stirred at that temperature for 1.5 h and filtered. The crystals were washed portionwise with 1.1 L isopropanol and dried for 72 h at 45° C./20 mbar, to give 583 g of the product as white crystals (100% yield; assay: 99.0%)

It is to be understood that the invention is not limited to the particular embodiments of the invention described above, as variations of the particular embodiments may be made and still fall within the scope of the appended claims.

What is claimed is:

1. A process for the preparation of (S)-4-fluoromethyl-dihydro-furan-2-one of the formula

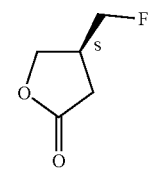

I comprising the step of converting a 4-fluoromethyl-5H-furan-2-one of the formula

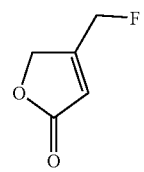

III by way of a catalytic asymmetric hydrogenation in the presence of a chiral catalyst, wherein the chiral catalyst is a ruthenium or a rhodium complex catalyst containing a chiral diphosphine ligand selected from the group consisting of formula IV, V, VI, VII and VIII:

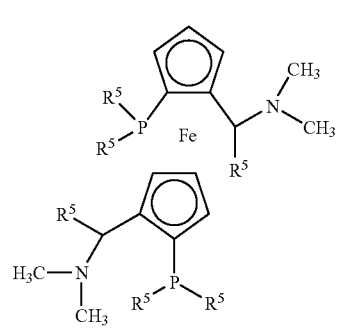

IV

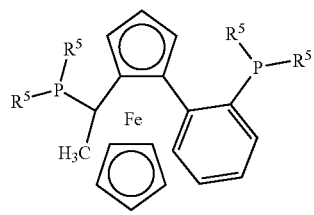

V

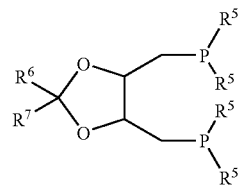

VI

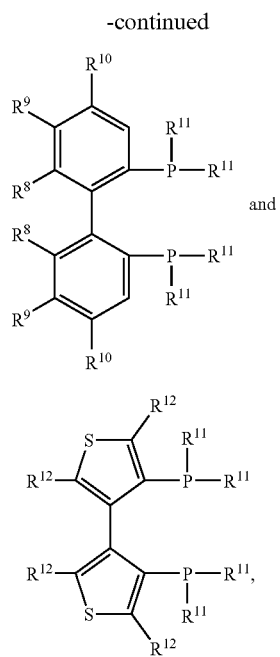

wherein
- R⁵ independently from each other is aryl, heteroaryl, cylcoalkyl or lower alkyl;
- R⁶ is lower alkyl;
- R⁷ is lower alkyl;
- R⁸ is lower alkyl, lower alkoxy, hydroxy or —O—C(O)-lower alkyl;
- R⁹ and R¹⁰ independently from each other are hydrogen, lower alkyl, lower alkoxy or lower dialkylamino; or
- R⁸ and R⁹ which are attached to the same phenyl group, or R⁹ and R¹⁰ which are attached to the same phenyl group, or both R⁸, taken together, are —X—(CH₂)ₙ—Y—, wherein X is —O— or —C(O)O—, Y is —O— or N(lower alkyl)- and n is an integer from 1 to 6; or
- R⁸ and R⁹, or R⁹ and R¹⁰, together with the carbon atoms to which they are attached, form a naphthyl, tetrahydronaphthyl or dibenzofuran ring;
- R¹¹ independently from each other is selected from the group consisting of unsubstituted phenyl,
- phenyl substituted by 1 to 5 substituents independently selected from the group consisting of lower alkyl, lower alkoxy, lower dialkylamino, morpholino, phenyl and lower trialkylsilyl,
- unsubstituted naphthyl, and
- napthyl substituted by 1 to 7 substituents independently selected from the group consisting of lower alkyl, lower alkoxy, lower dialkylamino, morpholino, phenyl and lower trialkylsilyl; and
- R¹² independently from each other is lower alkyl.

2. The process according to claim 1, wherein the chiral catalyst is a rhodium complex catalyst containing a chiral diphosphine ligand selected from the group consisting of
(S)-(+)-TMBTP, (S)-BINAP, (S)-MeOBIPHEP, (S)-BIPHEMP, (S)-Synphos, (S)-Solphos, (S)-(3-Thienyl)-MeOBIPHEP, (S)-3,5-tBu-MeOBIPHEP, (S)-3,5-Xyl-MeOBIPHEP, (S,S)-DIOP, (S,R)-NMe₂-PPh₂-Mandyphos, and (S)-(S)-Walphos.

3. The process according to claim 1, wherein the chiral catalyst is a ruthenium complex catalyst containing a chiral diphosphine ligand selected from the group consisting of
(R)-BINAP, (R)-p-Tol-BINAP, (R)-MeOBIPHEP, (R)-BIPHEMP, (R)-BIPHOMP, (R)-DiMeOBIPHEP, (R)-3,5-tBu-MeOBIPHEP, (R)-BIBFUP, (R)-3,5-tBu, 4-MeO-MeOBIPHEP, (R)-3,5-iPr-MeOBIPHEP, (R)-3,5-iPr, 4-MeO-MeOBIPHEP, and (R)-(3,5-Xyl-MeOBIPHEP) (S)-DAIPEN.

4. The process according to claim 1, wherein the chiral catalyst is a rhodium catalyst containing (S)-(+)-TMBTP as chiral diphosphine ligand.

5. The process according to claim 1, wherein the chiral catalyst is a ruthenium catalyst containing (R)-3,5-tBu-MeO-BIPHEP as chiral diphosphine ligand.

6. The process according to claim 1, wherein the chiral catalyst is a ruthenium catalyst containing (R)-3,5-iPr-MeO-BIPHEP as chiral diphosphine ligand.

7. The process according to claim 1, wherein the chiral catalyst is a ruthenium catalyst containing (R)-3,5-iPr, 4-MeO-MeOBIPHEP as chiral diphosphine ligand.

8. The process according to claim 1, wherein the asymmetric hydrogenation is carried out in an inert organic solvent.

9. The process according to claim 1, wherein the asymmetric hydrogenation is carried out in an inert organic solvent selected from the group consisting of dichloromethane, methanol, ethanol, n-propanol, isopropanol, 2,2,2-trifluoroethanol, benzotrifluoride, tetrahydrofuran, ethyl acetate and toluene.

10. The process according to claim 1, wherein the asymmetric hydrogenation is carried out in dichloromethane or benzotrifluoride.

11. The process according to claim 1, wherein the asymmetric hydrogenation is carried out in 2,2,2-trifluoroethanol or methanol.

12. The process according to claim 1, wherein the asymmetric hydrogenation takes place at a hydrogen pressure from 1 bar to 120 bar.

13. The process according to claim 1, wherein the asymmetric hydrogenation takes place at a hydrogen pressure from 1 bar to 20 bar.

14. The process according to claim 1, wherein the asymmetric hydrogenation takes place at a reaction temperature from 0° C. to 120° C.

15. The process according to claim 1, wherein the asymmetric hydrogenation takes place at a reaction temperature from 20° C. to 70° C.

16. A compound of the formula

17. The compound according to claim 16, wherein said compound is a component of an enantiomeric mixture of (S)- and (R)-4-fluoromethyl-dihydro-furan-2-one having an enantiomeric ratio of the (S)- to (R)-isomer of at least 70:30.

18. The compound according to claim 16, wherein said compound is a component of an enantiomeric mixture of (S)- and (R)-4-fluoromethyl-dihydro-furan-2-one having an enantiomeric ratio of the (S)- to (R)-isomer of at least 90:10.

19. A compound of the formula

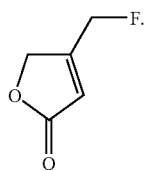
III

20. A process for the preparation of pyrido[2,1-a]isoquinoline derivatives of the formula

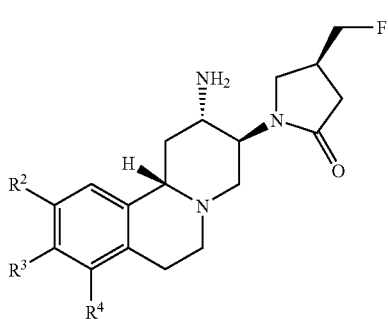
II wherein $R^2$, $R^3$ and $R^4$ are each independently selected from the group consisting of hydrogen, halogen, hydroxy, lower alkyl, lower alkoxy and lower alkenyl, wherein lower alkyl, lower alkoxy and lower alkenyl may optionally be substituted by a group selected from lower alkoxycarbonyl, aryl and heterocyclyl, comprising the process according to claim 1, followed by
a) coupling of the (S)-4-fluoromethyl-dihydro-furan-2-one of formula

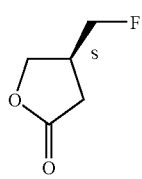
I with an amino-pyrido[2,1-a]isoquinoline derivative of formula

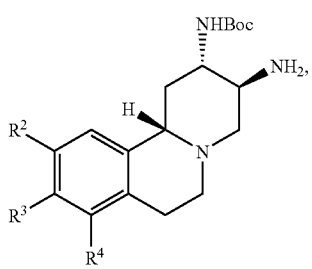
XIII wherein $R^2$, $R^3$ and $R^4$ are as defined above, b) cyclization of the obtained amide of formula

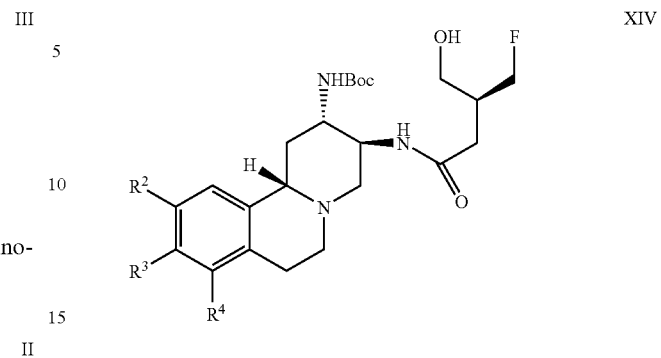
XIV in the presence of a base to obtain a compound of formula

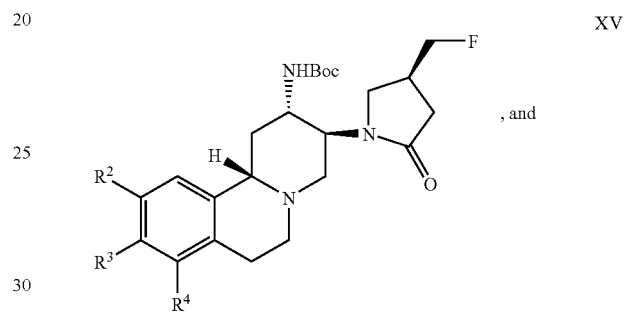
XV

, and c) deprotection of the amino group.

21. The process according to claim 20 for the preparation of (S)-1-((2S,3S,11bS)-2-amino-9,10-dimethoxy-1,3,4,6,7,11b-hexahydro-2H-pyrido[2,1-a]isoquinolin-3-yl)-4-fluoromethyl-pyrrolidin-2-one, comprising the process according to claim 1, followed by a) coupling of the (S)-4-fluoromethyl-dihydro-furan-2-one of formula

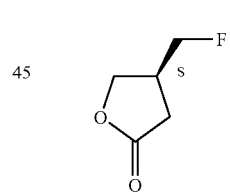
I with (2S,3S,11bS)-3-amino-9,10-dimethoxy-1,3,4,6,7,11b-hexahydro-2H-pyrido[2,1-a]isoquinolin-2-yl)-carbamic acid tert-butyl ester, b) cyclization of the obtained (2S,3S,11bS)-3-(3-fluoromethyl-4-hydroxy-butyrylamino)-9,10-dimethoxy-1,3,4,6,7,11b-hexahydro-2H-pyrido[2,1-a]isoquinolin-2-yl]-carbamic acid tert-butyl ester in the presence of a base, and c) deprotecting the obtained (2S,3S,11bS)-3-((4S)-fluoromethyl-2-oxo-pyrrolidin-1-yl)-9,10-dimethoxy-1,3,4,6,7,11b-hexahydro-2H-pyrido[2,1-a]isoquinolin-2-yl]-carbamic acid tert-butyl ester.

* * * * *

UNITED STATES PATENT AND TRADEMARK OFFICE
CERTIFICATE OF CORRECTION

| | | |
|---|---|---|
| PATENT NO. | : 7,619,101 B2 | Page 1 of 1 |
| APPLICATION NO. | : 11/438034 | |
| DATED | : November 17, 2009 | |
| INVENTOR(S) | : Stefan Abrecht et al. | |

It is certified that error appears in the above-identified patent and that said Letters Patent is hereby corrected as shown below:

In claim 21, Column 40, Line 52, please delete "(28, 38, 11bS)" and
Insert --(2S, 3S, 11bS)--

In claim 21, Column 40, Line 55, please delete "(28, 38, 11bS)" and
Insert --(2S, 3S, 11bS)--

In claim 21, Column 40, Line 60, please delete "(28, 38, 11bS)" and
Insert --(2S, 3S, 11bS)--

Signed and Sealed this

Twelfth Day of January, 2010

David J. Kappos
*Director of the United States Patent and Trademark Office*